(12) United States Patent
Lee et al.

(10) Patent No.: US 10,895,532 B2
(45) Date of Patent: *Jan. 19, 2021

(54) AIRBORNE MICROORGANISM MEASUREMENT DEVICE AND AIR CONDITIONING DEVICE INCLUDING THE SAME

(71) Applicant: LG ELECTRONICS INC., Seoul (KR)

(72) Inventors: Sujin Lee, Seoul (KR); Bongjo Sung, Seoul (KR); Ilna Son, Seoul (KR); Sanggu Lee, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/472,411

(22) PCT Filed: Dec. 6, 2017

(86) PCT No.: PCT/KR2017/014264
§ 371 (c)(1),
(2) Date: Jun. 21, 2019

(87) PCT Pub. No.: WO2018/117492
PCT Pub. Date: Jun. 28, 2018

(65) Prior Publication Data
US 2019/0360935 A1 Nov. 28, 2019

(30) Foreign Application Priority Data

Dec. 21, 2016 (KR) .................. 10-2016-0175860
Dec. 21, 2016 (KR) .................. 10-2016-0175861
Dec. 21, 2016 (KR) .................. 10-2016-0175862

(51) Int. Cl.
*G01N 21/64* (2006.01)
*G01N 21/47* (2006.01)
(Continued)

(52) U.S. Cl.
CPC ............. *G01N 21/64* (2013.01); *G01N 21/47* (2013.01); *G01N 21/94* (2013.01); *F24F 11/30* (2018.01); *G01N 1/24* (2013.01); *G01N 33/483* (2013.01)

(58) Field of Classification Search
CPC .. G01N 21/6486; G01N 21/64; G01N 21/645; G01N 2015/0046;
(Continued)

(56) References Cited

U.S. PATENT DOCUMENTS 5,442,190 A 8/1995 Leck
5,949,001 A * 9/1999 Willeke ............. G01N 15/0255
356/336
(Continued)

FOREIGN PATENT DOCUMENTS

EP 1 607 692 12/2005
EP 2 816 846 12/2014
(Continued)

OTHER PUBLICATIONS

International Search Report (with English Translation) and Written Opinion dated Mar. 26, 2018 issued in Application No. PCT/KR2017/014264.
(Continued)

*Primary Examiner* — Hoa Q Pham
(74) *Attorney, Agent, or Firm* — Ked & Associates LLP

(57) ABSTRACT

An airborne microorganism measurement device includes a housing including a first body and a second body, an air passage formed between the first body and the second body such that air containing airborne microorganisms pass there-
(Continued)

through, a charging part and a collecting part disposed in the air passage to charge and collect the airborne microorganisms, a high voltage generating device provided in the first body to supply a high voltage to the charging part and the collecting part, and a light emitting unit and a light receiving part provided in the second body to detect a fluorescent signal generated by irradiating the airborne microorganisms collected in the collecting unit with light.

20 Claims, 15 Drawing Sheets

(51) Int. Cl.
  *G01N 21/94* (2006.01)
  *F24F 11/30* (2018.01)
  *G01N 1/24* (2006.01)
  *G01N 33/483* (2006.01)

(58) Field of Classification Search
  CPC ..... G01N 2201/061; G01N 2201/0686; G01N 2021/6463; G01N 2021/6421; G01N 15/0606; G01N 15/0612; G01N 15/10; G01N 21/6428; G01N 33/0036; C12Q 1/04; F24F 11/0017; F24F 13/20
  USPC ........ 356/335–343, 73, 36; 250/458.1, 462.1
  See application file for complete search history.

(56) References Cited

U.S. PATENT DOCUMENTS

| | | | | |
|---|---|---|---|---|
| 7,799,567 | B1* | 9/2010 | Call | B07B 7/00 436/174 |
| 8,372,183 | B2 | 2/2013 | Doucette et al. | |
| 8,872,653 | B2* | 10/2014 | Okuno | C12Q 1/06 340/539.1 |
| 8,901,512 | B2* | 12/2014 | Fujita | G01N 21/6486 250/458.1 |
| 9,700,920 | B2* | 7/2017 | Kamo | A46B 3/08 |
| 9,976,957 | B2* | 5/2018 | Kim | F24F 1/0007 |
| 2003/0121278 | A1 | 7/2003 | Ichimura et al. | |
| 2005/0105079 | A1 | 5/2005 | Pletcher et al. | |
| 2005/0190058 | A1 | 9/2005 | Call | |
| 2007/0013910 | A1 | 1/2007 | Jiang et al. | |
| 2007/0188760 | A1 | 8/2007 | Bouzid | |
| 2011/0204220 | A1* | 8/2011 | van Wuijckhuijse | H01J 49/164 250/282 |
| 2012/0161033 | A1 | 6/2012 | Kwon et al. | |
| 2012/0257192 | A1 | 10/2012 | Jiang | |
| 2012/0307234 | A1 | 12/2012 | Jiang et al. | |
| 2012/0315666 | A1* | 12/2012 | Fujioka | G01N 15/0612 435/39 |
| 2014/0078500 | A1 | 3/2014 | Jiang et al. | |
| 2015/0001405 | A1* | 1/2015 | Fujita | B03C 3/47 250/365 |
| 2015/0177143 | A1* | 6/2015 | Fujita | G01N 15/0612 250/458.1 |
| 2017/0165606 | A1* | 6/2017 | Lee | A61L 9/22 |
| 2018/0058930 | A1* | 3/2018 | Ramer | G01J 3/10 |

FOREIGN PATENT DOCUMENTS

| | | |
|---|---|---|
| JP | 2009-526993 | 7/2009 |
| JP | 2012-251889 | 12/2012 |
| JP | 2013-068595 | 4/2013 |
| JP | 2014-025876 | 2/2014 |
| KR | 10-2004-0107900 | 12/2004 |
| KR | 10-2006-011669 | 11/2006 |
| KR | 10-2007-0045214 | 5/2007 |
| KR | 10-2011-0009472 | 1/2011 |
| KR | 10-2012-0071453 | 7/2012 |
| KR | 10-1163641 | 7/2012 |
| KR | 10-1355301 | 1/2014 |
| KR | 10-2014-0016923 | 2/2014 |
| KR | 10-1418295 | 7/2014 |
| WO | WO 2012/165036 | 12/2012 |

OTHER PUBLICATIONS

European Search Report dated Jul. 13, 2020 issued in EP Application No. 17884740.6.

* cited by examiner

FIG. 10

```
START
  ↓
TURN ON POWER SUPPLY — S10
  ↓
CLEAN COLLECTING PART — S20
  ↓
COLLECT AIRBORNE MICROORGANISMS IN COLLECTING PART — S30
  ↓
RADIATE LIGHT TO PREDETERMINED WAVELENGTH REGION THROUGH LIGHT EMITTING UNIT — S40
  ↓
DETECT FLUORESCENT SIGNAL THROUGH LIGHT RECEIVING PART — S50
  ↓
DISPLAY CONCENTRATION OF AIRBORNE MICROORGANISMS — S60
  ↓
TURN OFF POWER SUPPLY — S70
  ↓
END
```

AIRBORNE MICROORGANISM MEASUREMENT DEVICE AND AIR CONDITIONING DEVICE INCLUDING THE SAME

CROSS-REFERENCE TO RELATED PATENT APPLICATIONS

This application is a U.S. National Stage Application under 35 U.S.C. § 371 of PCT Application No. PCT/KR2017/014264, filed Dec. 6, 2017, which claims priority to Korean Patent Application Nos. 10-2016-0175860, 10-2016-0175861 and 10-2016-0175862, all filed Dec. 21, 2016, whose entire disclosures are hereby incorporated by reference.

TECHNICAL FIELD

The present invention relates to an airborne microorganism measurement device and an air conditioning device including the same.

BACKGROUND ART

In recent years, indoor air pollution has become increasingly serious as the introduction of external gas is minimized and airtightness is made to save energy. Accordingly, various legal regulations on indoor pollutants are gradually strengthened.

The indoor pollutants may include (1) particulate pollutants such as fine dust or asbestos, (2) gaseous pollutants such as carbon dioxide, formaldehyde, or volatile organic compounds (VOC), and (3) biological contaminants such as viruses, fungi, or bacteria.

In particular, the biological contaminants may adversely affect the health of a user. In recent years, technologies for measuring the amount of such biological contaminants and purifying the indoor air based on the measured amount have been developed.

The prior art information related to these technologies is as follows.

(1) First Prior Art Document: Registered patent 10-1163641 (registered on Jul. 2, 2012), entitled "device AND MATHOD FOR MEASUREING AIRBORNE MICROORGANISMS IN GAS PHASE IN REAL TIME USING MICROBIAL DISSOLUTION SYSTEM".

The first prior art document is characterized to include a collecting part in which airborne microorganisms are collected and ATP (Adenosine triphosphate) reactive luminescent agent is present, a microbial dissolution system capable of extracting the ATP, and a light receiving part for detecting light generated when the ATP extracted by the microbial dissolution system reacts with the ATP reactive luminescent agent.

(2) Second Prior Art Document: Registered patent 10-1355301 (registered on Jan. 17, 2014) entitled "DETECTION APPARATUS AND DETECTION METHOD FOR DETECTING BIOLOGICAL PARTICLES IN AIR".

The detection device of the second prior art document includes a light emitting element, a light receiving element for receiving fluorescence, and a calculation unit for calculating the amount of airborne microorganism particles in air based on the amount of fluorescence received by the light receiving element when light irradiated from the light emitting element is irradiated to air introduced into the detection device.

According to the conventional airborne microorganism measurement device according to the prior art documents, the following problems arise.

(1) Conventional airborne microorganisms measurement devices require a somewhat complicated structure and a large number of parts, and expensive laser and lenses are used to require a large amount of costs to manufacture the device.

(2) Since the conventional airborne microorganism measurement device is bulky and needs to be located in a specific place as a single device, there is a problem that it is limited to be included in a specific household appliance or a portable device.

(3) Further, in order to measure the amount or concentration of the airborne microorganisms, it has been difficult to perform a separate fluorescence treatment on the airborne microorganisms or use luminescent agent.

(4) In addition, since light cannot be transmitted through the collecting substrate to cause noise, the fluorescence signal cannot be measured in the light receiving part.

(5) Further, since the collecting substrate must be replaced after measuring the airborne microorganisms collected in the collecting substrate, the replacement time is increased and the cost is increased excessively.

DISCLOSURE

Technical Problem

In order to solve such a problem, an object of embodiments is to provide an airborne microorganism measurement device capable of being installed in an air conditioning device, which is realized in a miniaturized and simplified structure.

Another object of embodiments is to provide an airborne microorganism measurement device capable of being implemented with a simple structure and being miniaturized to be mounted on another product or manufactured in a portable type.

Technical Solution

According to an aspect, an airborne microorganism measurement device includes a housing including a first body and a second body, an air passage formed between the first body and the second body such that air containing airborne microorganisms pass through, a charging part and a collecting part disposed in the air passage to charge and collect the airborne microorganisms, a high voltage generating device provided in the first body to supply a high voltage to the charging part and the collecting part, and a light emitting unit and a light receiving part provided in the second body to detect a fluorescent signal generated by irradiating the airborne microorganisms collected in the collecting unit with light.

The charging part may be disposed adjacent to a first opening of the air passage into which the air containing the airborne microorganisms is introduced, and the collecting part may be disposed adjacent to a second opening of the air passage to collect the airborne microorganisms charged by the charging part.

The collecting part may include a collecting substrate connected to the high voltage generator and disposed in the air passage abutting the first body.

The collecting substrate may be made of a glass member having electrical conductivity.

The charging part may include a high voltage wire connected to the high voltage generator and a pair of ground plates facing each other with the high voltage wire as a center.

The second body may be formed with an incident light passage and a light receiving passage which are connected to the air passage, the light emitting unit may be disposed in the incident light passage, and the light receiving part may be disposed in the light receiving passage.

The incident light passage may be formed along a first path of light directed from the light emitting unit toward one point of the collecting part, and the light receiving passage may be formed along a second path of a fluorescent signal directed from one point of the collecting part toward the light receiving part.

The first path and the second path may form a predetermined path angle (θ).

The airborne microorganism measurement device may further include a cleaning part of which at least a part is disposed in the first body to remove the airborne microorganisms collected in the collecting part.

The first body may include a first space portion and a second space portion, the high voltage generator may be disposed in the first space portion, and the at least a part of the cleaning part may be disposed in the second space portion.

The first space portion may be positioned adjacent to the charging part, and the second space portion may be positioned adjacent to the collecting part.

The cleaning part may include a removing part configured to move in contact with the collecting substrate, and a motor configured to transfer power to the removing part.

The removing part may be arranged to move between a first side and a second side of the collecting substrate to remove collected airborne microorganisms.

At least one of the first side and the second side may be provided with a treatment part for treating the airborne microorganisms removed by the removing part.

In addition, according to another aspect, an airborne microorganism measurement device includes a measurement plate configured to accommodate a measurement object, a light emitting unit configured to radiate light of a predetermined wavelength region to the measurement plate, a first light receiving filter provided on one side of the measurement plate and disposed such that the target signal passes through, a light receiving lens provided on one side of the first light receiving filter to collect the target signal having passed through the first light receiving filter, a first light receiving filter provided on one side of the light receiving lens and disposed such that the target signal collected by the light receiving lens passes through, and a light receiving part provided on one side of the second light receiving filter to detect the target signal having passed through the second light receiving filter.

The first light receiving filter may be configured to pass light having a first wavelength or longer and the second light receiving filter may be configured to pass light having a second wavelength or longer, and the first wavelength and the second wavelength may be different from each other.

The airborne microorganism measurement device may further include an optical housing in which the light emitting unit, the measurement plate, the first light receiving filter, the light receiving lens, the second light receiving filter, and the light receiving part are installed, and the first light receiving filter, the light receiving lens, the second light receiving filter, and the light receiving part may be sequentially arranged in a light receiving passage formed in the optical housing.

According to still another aspect, an airborne microorganism measurement device includes a housing provided with a first opening and a second opening, an air passage formed to pass through the housing to connect the first opening and the second opening, a charging part disposed in the air passage adjacent to the first opening to charge airborne microorganisms in air introduced into the air passage through the first opening, and a collecting part disposed in the air passage adjacent to the second opening to collect the charged airborne microorganisms moving along the air passage through the charging part, wherein a width of the air passage is formed to become narrower from the first opening toward the second opening.

The air passage may have a width of 4 mm or more and 6 mm or less.

According to an aspect, an air conditioning device includes an airborne microorganism measurement device.

Advantageous Effects

According to the proposed embodiment, a small-sized airborne microorganism measurement device can be provided and installed in an air conditioning device, and the concentration of airborne microorganisms in air sucked into the air conditioner can be easily measured.

In addition, since a path of light directed from the light emitting unit to the collecting substrate and a path of light directed from the collecting substrate to the light receiving part are formed to be short, thereby improving the collection rate of the fluorescent signals emitted from the airborne microorganisms.

In addition, the fluorescence signals may be realized by using the absorption or luminescence phenomenon of riboflavin contained in the airborne microorganisms without requiring a separate fluorescence treatment for the airborne microorganisms, thereby simplifying the measurement process through the airborne microorganism measurement device.

In addition, since the light receiving part includes a device capable of detecting only the emission wavelength band region of the riboflavin, it is possible to relatively accurately measure the amount of the airborne microorganisms without measuring the scattered light such as fine dust contained in the flowing air.

In addition, since the light emitting unit is formed using a laser diode which is less expensive than the conventional light source (light emitting unit), the manufacturing cost of the device can be reduced.

In addition, the collecting plate is made of an electrically conductive and transparent glass material, thereby enhancing the light transmittance and reducing the noise.

In addition, a cleaning part for cleaning the collecting substrate in which airborne microorganisms are collected is provided, which is advantageous in that the collecting substrate can be used semi-permanently.

DESCRIPTION OF DRAWINGS

FIG. 10 is a control flowchart of an airborne microorganism measurement device according to an embodiment of the present invention.

MODE FOR INVENTION

Hereinafter, specific embodiments of the present invention will be described with reference to the drawings. It is to be understood, however, that the spirit of the invention is not limited to the embodiments shown and that those skilled in the art, upon reading and understanding the spirit of the invention, may easily suggest other embodiments within the scope of the same concept.

Figure 1:
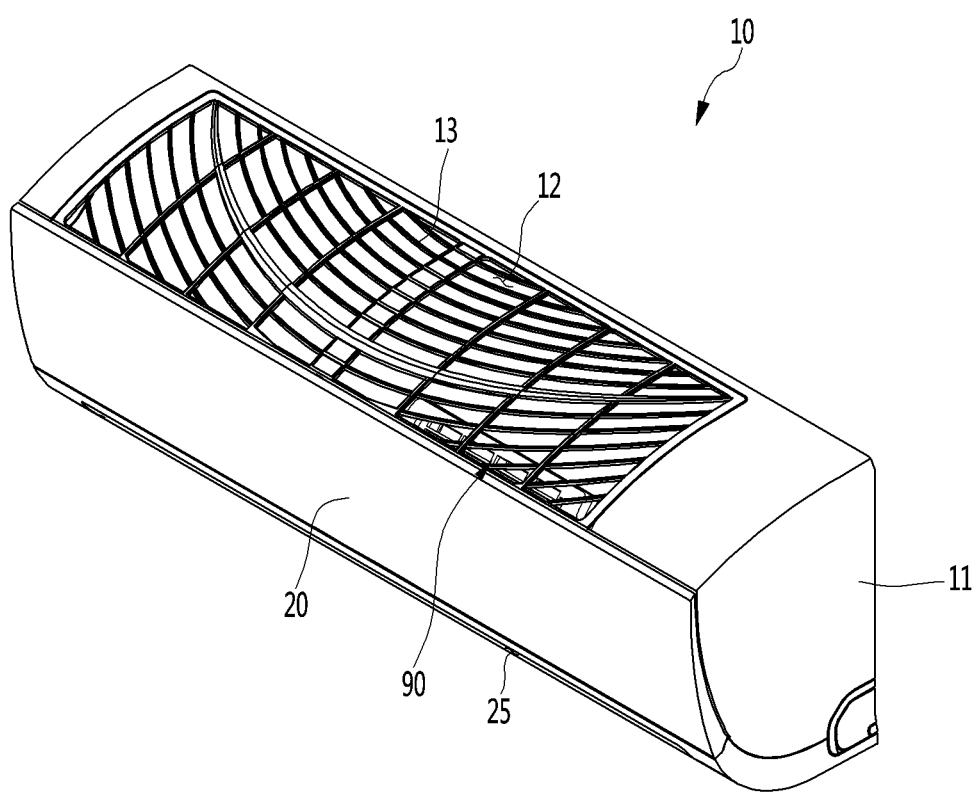
FIG. 1 is a perspective view showing a configuration of an air conditioning device according to an embodiment of the present invention.
Figure 2:
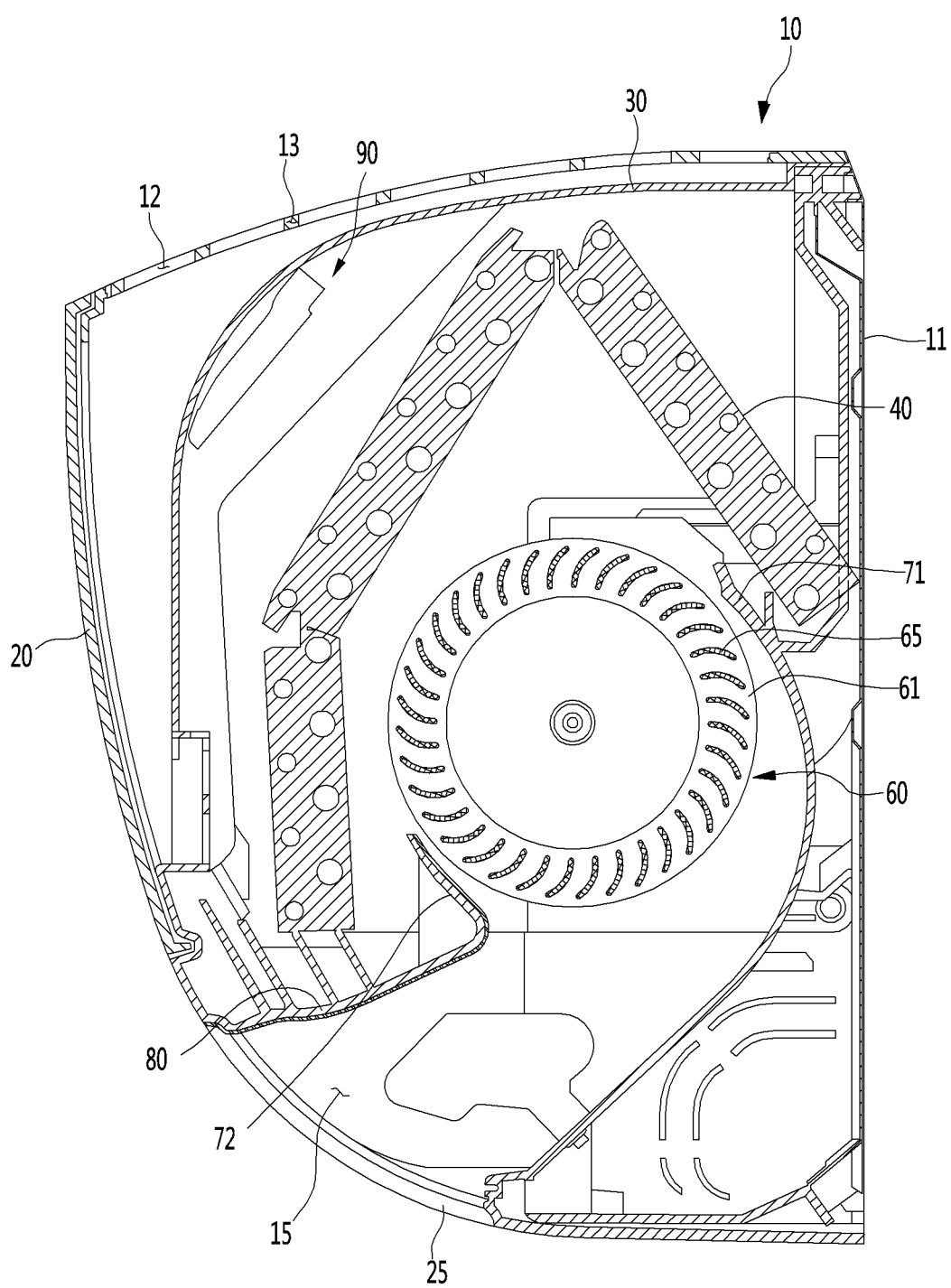
FIG. 2 is a cross-sectional view showing a configuration of an air conditioning device according to an embodiment of the present invention.

FIG. 1 is a perspective view showing a configuration of an air conditioning device according to an embodiment of the present invention, and FIG. 2 is a cross-sectional view showing a configuration of an air conditioning device according to an embodiment of the present invention.

Referring to FIGS. 1 and 2, an air conditioning device according to an embodiment of the present invention may include an air conditioner 10 capable of cooling, heating, or air cleaning operations. Although the air conditioner 10 is described as an example of the air conditioning device in the present embodiment, the air conditioner may be equipped with an airborne microorganism measurement device according to the present embodiment.

In detail, the air conditioner 10 may include a case 11 forming an appearance and having a heat exchanger 40 and a blowing fan 60 disposed thereon, and a front panel 20 coupled to the front of the case 11 to form a front appearance of the air conditioner 10.

The case 11 may be a case of an indoor unit disposed in a room in the case of a split air conditioner, or may be a case of an air conditioner itself in the case of an integrated air conditioner. In a broad sense, the front panel 20 may be understood as a configuration of the case 11.

The case 11 may include a suction portion 12 through which indoor air is introduced and a discharge portion 15 through which the air introduced through the suction portion 12 is heat-exchanged and discharged into an indoor space. The suction portion 12 may be formed in such a way that at least a portion of the upper portion of the case 11 is opened and the discharge portion 15 may be formed in such a way that at least a portion of the lower portion of the case 11 is opened. The suction portion 12 is formed with a suction grill 13 for preventing foreign matters from being introduced into the suction portion 12 and a discharge grill (not shown) may be provided in the discharge portion 15.

A discharge vane 25 which is movably provided to open or close the discharge portion 15 may be included on a side of the discharge portion 15. When the discharge vane 25 is opened, air conditioned inside the case 11 may be discharged to the indoor space. For example, the discharge vane 25 may be opened by rotating a lower portion of the discharge vane 25 upward.

A heat exchanger 40 for heat exchange with the air sucked through the suction portion 12 is installed in the case 11. The heat exchanger 40 may include a refrigerant tube through which refrigerant flows, and heat exchange fins coupled with the refrigerant tube to increase a heat exchange area.

The heat exchanger 40 may be disposed so as to surround the suction side of the blowing fan 60. For example, the heat exchanger 40 may include a plurality of bent heat exchangers.

The blowing fan 60 may include a cross flow fan for discharging air, sucked in the circumferential direction, in the circumferential direction. The blowing fan 60 may include a fan body 61 as a fixing member and a plurality of blades 65 fixed to one side of the fan body 61 and spaced apart from one another in the circumferential direction. That is, the plurality of blades 65 are arranged in the circumferential direction.

In the case 11, there are provided flow guides 71 and 72 which are arranged near the outer circumferential surface of the blowing fan 60 to guide air flow. The flow guides 71 and 72 include a rear guide 71 and a stabilizer 72.

The rear guide 71 extends from the rear side of the case 11 to the suction side of the blowing fan 60. The rear guide 71 guides the sucked air to the blowing fan 60 smoothly when the blowing fan 60 is rotated. Further, the rear guide 71 may prevent air flowing by the blowing fan 60 from being peeled off from the blowing fan 60.

The stabilizer 72 is disposed on the discharge side of the blowing fan 60. The stabilizer 72 is spaced apart from the outer circumferential surface of the blowing fan 60 to prevent air discharged from the blowing fan 60 from flowing back to the heat exchanger 40. The rear guide 71 and the stabilizer 72 extend in the longitudinal direction of the blowing fan 60.

A drain portion 80 is provided below the heat exchanger 40 to store condensed water generated during heat exchange between air and refrigerant.

A filter 30 for filtering out foreign matters in air sucked through the suction portion 12 is provided inside the case 11. The filter 30 is arranged to surround the heat exchanger 40 inside the suction portion 12. Air filtered by the filter 30 may flow toward the heat exchanger 40.

An airborne microorganism measurement device case 90 may be installed on one side of the filter 30. For example, the airborne microorganism measurement device case 90 is installed on the outlet side of the filter 30, so that at least a part of the air filtered by the filter 30 is introduced into the case 90 of the airborne microorganism measurement device.

Figure 3:
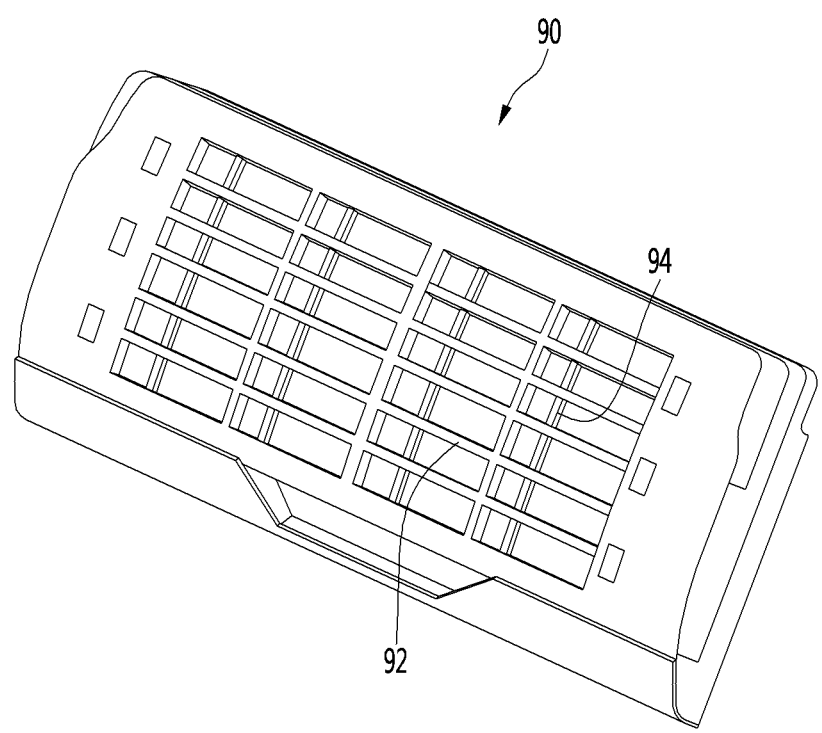
FIG. 3 is a perspective view showing a configuration of a case of an airborne microorganism measurement device according to an embodiment of the present invention.

FIG. 3 is a perspective view showing a configuration of the airborne microorganism measurement device case 90 according to an embodiment of the present invention.

The airborne microorganism measurement device case 90 includes an inflow portion 92 through which at least a part of air passing through the filter 30 is introduced and an outflow portion 94 through which the air is discharged.

An airborne microorganism measurement device 100 is disposed inside the airborne microorganism measurement device case 90. The airborne microorganism measurement device 100 may be configured to measure the amount or concentration of airborne microorganisms contained in air. A configuration of the airborne microorganism measurement device 100 will be described below with reference to the drawings.

Figure 4:
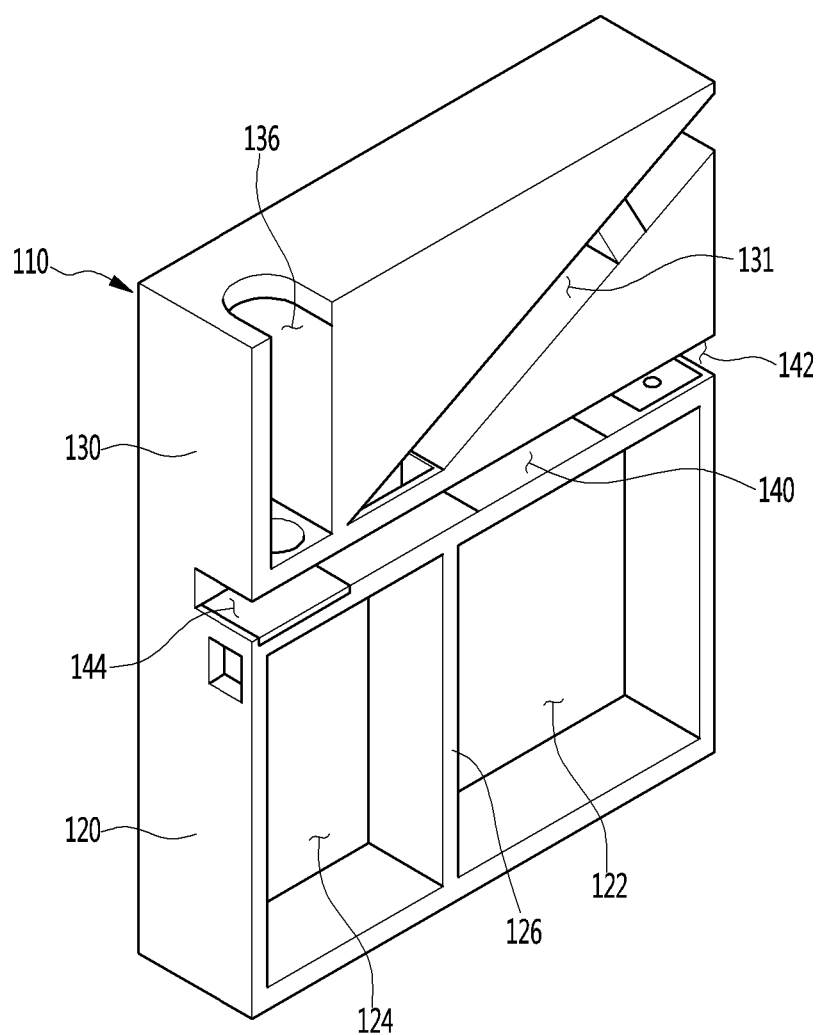
FIG. 4 is a perspective view showing a configuration of an airborne microorganism measurement device according to an embodiment of the present invention.

FIG. 4 is a perspective view showing a configuration of the airborne microorganism measurement device 100 according to an embodiment of the present invention.

The airborne microorganism measurement device 100 is provided in the form of a housing 110 in which various device s are installed. For convenience of description, various device s installed in the housing 110 are not shown in FIG. 4. In addition, for the sake of illustration of an internal structure, a cover covering a front surface of the housing 110 is omitted in FIG. 4.

The housing 110 includes a first body 120 and a second body 130 spaced apart from one side of the first body 120 and an air passage 140 formed between the first body 120 and the second body 130. Referring to FIG. 4, the second body 130 may be disposed above the first body 120.

Further, the housing 110 also includes a first opening 142 and a second opening 144 spaced apart from the first opening 142. The air passage 140 is formed to pass through the housing 110 such that the first opening 142 and the second opening 144 are connected to each other. Air having passed through the filter 30 may flow through the air passage 140.

The first body 120 includes a first space portion 122 and a second space portion 124 in which various device s may be accommodated, and a separating wall 126 for separating the first space portion 122 from the second space portion 124. Referring to FIG. 4, the first space portion 122 may be disposed on the right side of the second space portion 124.

The second body 130 is formed with an incident light passage 131 and a light receiving passage 136 which are connected to at least a part of the air passage 140. The incident light passage 131 and the light receiving passage 136 are formed to pass from one side of the air passage 140 to one side of the outer side of the housing 110.

As shown in FIG. 4, each of the incident light passage 131 and the light receiving passage 136 may form a predetermined path angle θ with respect to the one side of the air passage 140. Details will be described later.

In summary, the housing 110 includes the first body 120 and the second body 130 disposed on both sides of the air passage 140, the first body 120 are provided with the first space portion 122 and the second space portion 124, and the second body 130 are formed with the incident light passage 131 and the light receiving passage 136.

Various device s installed in the housing 110 will be described below based on the structure of the housing 110 described above.

Figure 5:
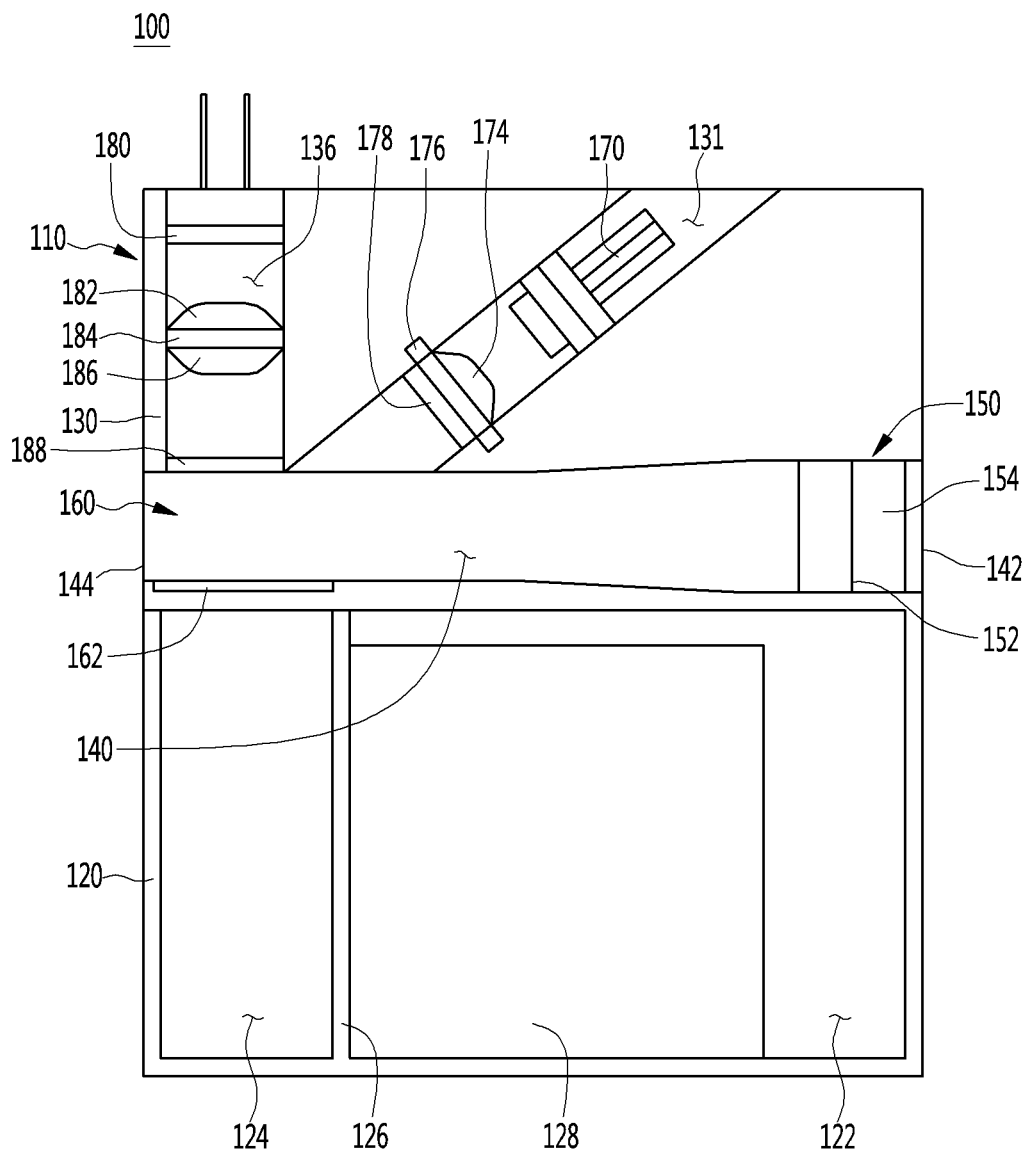
FIG. 5 is a plan view showing a configuration of an airborne microorganism measurement device according to an embodiment of the present invention.

FIG. 5 is a plan view showing a configuration of an airborne microorganism measurement device 100 according to an embodiment of the present invention.

As described above, air containing airborne microorganisms having passed through the filter 30 may flow through the air passage 140. The air is introduced into the air passage 140 through the first opening 142 and discharged from the air passage 140 through the second opening 144. That is, the first opening 142 is an 'inlet' of air and the second opening 144 is an 'outlet' of air.

In the air passage 140, there are installed a charging part 150 and a collecting part 160 spaced apart from the charging part 150. The charging part 150 is disposed adjacent to the first opening 142, through which air containing airborne microorganisms is introduced, to charge the airborne microorganisms. The collecting part 160 is disposed adjacent to the second opening 144 so as to collect the airborne microorganisms charged by the charging part 150. That is, the collecting part 160 is disposed on the rear side of the charging part 150 in the flow direction of air.

In this case, the first space portion 122 is adjacent to the first opening 142, and the second space portion 124 is adjacent to the second opening 144. That is, the first space portion 122 is adjacent to the charging part 150, and the second space portion 124 is adjacent to the collecting part 160.

A high voltage generator 128 for applying a high voltage to the charging part 150 and the collecting part 160 is disposed in the first space portion 122. The high voltage generator 128 may be connected to the charging part 150 and the collecting part 160 to apply high voltages of different polarities.

For example, the high voltage generator 128 may apply a positive (+) voltage to the charging part 150 and a negative (−) voltage to the collector part 160. Accordingly, airborne microorganisms in air introduced into the first opening 142 may pass through the charging part 150, be charged to the (+) polarity, and be collected in the collecting part 160 applied with the negative (−) voltage.

Specifically, the charging part 150 may include a high voltage wire 152 connected to the high voltage generator 128 and a pair of ground plates 154 facing each other with the high voltage wire 152 as a center.

Referring to FIG. 5, the high voltage wire 152 extends from an upper portion to a lower portion of the air passage 140, and the ground plates 154 are disposed on both sides of the high voltage wire 152. In FIG. 5, the one ground plate 154 disposed on the front side of the high voltage wire 152 is omitted for convenience of description.

This is exemplary, and the high voltage wire 152 and the ground plate 154 may be arranged in various ways. For example, the ground plates 154 may be respectively disposed in upper and lower portions of the air passage 140, and the high voltage wire 152 may extend to connect both sides of the air passage 140.

A specific high voltage is applied to the high voltage wire 152 by the high voltage generator 128 and a corona discharge may be generated due to a voltage difference between the high voltage wire 152 and the ground plate 154. The negative (−) ions or positive (+) ions generated during the corona discharge are charged with the airborne microorganisms in the air, and therefore, the airborne microorganisms may be charged.

The collecting part 160 includes a collecting substrate 162 connected to the high voltage generator 128 to collect the charged airborne microorganisms. As shown in FIG. 5, the collecting substrate 162 is disposed on one side of the air passage 140 that abuts the first body 120.

The collecting substrate 162 includes an electrically conductive glass member. In particular, the collecting substrate 162 may be a glass member coated with ITO (Indium Tin Oxide). Such an ITO glass member has high electrical conductivity and high light transmittance.

Since the collecting substrate 162 is made of a transparent or translucent material having high transmittance, a part of light irradiated by a light emitting unit 70, which will be described later, may be transmitted through the collecting substrate 162. Therefore, a rate of reflection of unnecessary light is reduced, thereby reducing noise and more accurately measuring airborne microorganisms.

In addition, the collecting substrate 162 may include a sapphire wafer. Since the sapphire wafer has a hydrophobic property, moisture contained in air may be prevented from being collected on the wafer 162. Since the sapphire wafer has a very high hardness, the sapphire wafer is characterized in that its abrasion is prevented.

Also, the width of the air passage 140 may be formed to be narrower from the first opening 142 toward the second opening 144. For example, the width of the air passage 140 adjacent to the first opening 142 may be 6 mm, and the width of the air passage 140 adjacent to the second opening 144 may be 4 mm. That is, the width of the air passage 140 may be 4 mm or more and 6 mm or less. That is, the first opening 142 may be larger than the second opening 144.

The structure of the air passage 140 is to improve the charging efficiency of the charging part 150 and the collection efficiency of the collecting part 160. In detail, a predetermined distance between the high voltage wire 152 and the ground plate 154 needs to be ensured such that a corona discharge is generated in the charging part 150. In addition, the charged airborne microorganisms may flow along the air passage 140 which becomes narrower and be collected, and thus may be collected more effectively on the collecting substrate 162.

As described above, the incident light passage 131 and the light receiving passage 136 are formed in the second body 130. The incident light passage 131 and the light receiving passage 136 communicate with the air passage 140 to be connected to the collecting part 160.

Specifically, the incident light passage 131 is provided with a light emitting unit 70 for irradiating light to airborne microorganisms collected in the collecting part 160. That is, the incident light passage 131 is formed along a first path L1 of light directing from the light emitting unit 70 toward one point of the collecting part 160.

The light emitting unit 70 includes a laser diode. The laser diode may emit light having a predetermined wavelength value or a wavelength region. For example, the light may have a wavelength value of 405 nm or have a wavelength region of 395 nm to 415 nm.

The output of the laser diode may have a value equal to or less than a set output. When the output of the laser diode is too high, the airborne microorganisms collected in the collecting part 160 may be destroyed before measurement. For example, the set output may be 20 mW.

The incident light passage 131 may be provided with an incident light lens 74 and an incident light filter 78. The incident light lens 74 and the incident light filter 78 may be supported on the incident light passage 131 by an incident light supporting portion 76. As shown in FIG. 5, the incident light lens 74 is provided on one side of the incident light supporting portion 76, and the incident light filter 78 is provided on the other side. The above-described configurations are exemplary, and the incident light lens 74 and the incident light filter 78 may be respectively supported by supporting portions or may be installed directly on the inner wall of the incident light passage 131.

The incident light lens 74 may be disposed on the exit side of the light of the light emitting unit 70 to collect light irradiated from the light emitting unit 70. For example, the light irradiated from the light emitting unit 70 has a divergence angle of about 10 degrees, and thus the light irradiated from the light emitting unit 170 has a gradually diverging path while traveling toward the collecting part 160. Therefore, the incident light lens 74 may be disposed on the exit side of the light emitting unit 70 to make the light parallel toward the collecting part 160.

The incident light filter 78 may be disposed on the exit side of the light of the light emitting unit 70 to perform a function of passing only light of a predetermined wavelength region of the light irradiated from the light emitting unit 70. For example, when light outside the predetermined wavelength region (395 to 415 nm) is irradiated from the light emitting unit 70, the light may be filtered out in the process of passing through the incident light filter 78. Further, a diffusion preventing portion (not shown) for preventing light scattering (diffusion phenomenon) may further be provided on the exit side of the incident light filter 178.

The light receiving part 180 for detecting a fluorescence signal generated from riboflavin contained in the airborne microorganisms collected in the collecting substrate 162 by the irradiated light is disposed in the light receiving passage 136. That is, the light receiving passage 136 is formed along a second path L2 of light directing from one point of the collecting part 160 to the light receiving part 180.

In this case, riboflavin is a coenzyme contained in the airborne microorganism, and generates a specific signal due to light irradiated from the light emitting unit 70. This is called a 'fluorescence signal', and airborne microorganisms may be measured by detecting such fluorescence signals. By measuring the riboflavin contained in the airborne microorganisms, airborne microorganisms may be measured without a separate fluorescence treatment.

The light receiving part 180 includes an element that receives the fluorescence signal of the riboflavin and has high sensitivity to light of a predetermined wavelength value or wavelength region. The predetermined wavelength value or wavelength region may be a value or region determined to detect only the emission wavelength of riboflavin contained in airborne microorganisms and not to measure the scattered light or the like of fine dust contained in air. For example, the predetermined wavelength value may be 565 nm, and the wavelength region may be 555 to 575 nm.

Also, the light receiving part 180 includes a photodiode, and the photodiode has a relatively short reaction time.

Further, a plurality of light receiving lenses 182 and 186 and a light receiving filter 188 may be provided in the light receiving passage 136. The light receiving lenses 182 and 186 and the light receiving filter 188 are disposed between the light receiving part 180 and the collecting part 160. That is, the light receiving lenses 182 and 186 and the light receiving filter 188 may be disposed on the entrance side of the light receiving part 180, respectively.

As shown in FIG. 5, the light receiving filter 188 may be disposed adjacent to the air passage 140. The light receiving filter 188 may function to selectively pass light of a wavelength region capable of being processed, among the fluorescent signals obtained from the airborne microorganisms. For example, the light receiving filter 188 may function to prevent a wavelength region of light irradiated from the light emitting unit 170 from passing therethrough. Therefore, the light reflected by the collecting part 160 and moving to the light receiving passage 136 among the light irradiated from the light emitting unit 170 may be filtered while passing through the light receiving filter 188.

The plurality of light receiving lenses 182 and 186 may be installed at the exit side of the light receiving filter 188, that is, at a position where the fluorescent signal having passed through the light receiving filter 188 may pass through.

The plurality of light receiving lenses include a first light receiving lens 182 and a second light receiving lens 186. The first light receiving lens 182 and the second light receiving lens 186 may be supported on the light receiving passage 184 by the light receiving supporting portion 184. As shown in FIG. 5, the first light receiving lens 182 is installed on one side of the light receiving supporting portion 184, and the second light receiving lens 186 is provided on the other side. The above-described configurations are exemplary, and the first light receiving lens 182 and the second light receiving lens 186 may be respectively supported by supporting portions or may be installed directly on the inner wall of the light receiving passage 136.

The first light receiving lens 182 and the second light receiving lens 186 function to allow a fluorescent signal having passed through the light receiving filter 188 to be focused.

The first and second light receiving lenses 182 and 186 may be composed of the same kind of lenses as a condensing lens. Since the plurality of light receiving lenses are provided, focusing of the fluorescence signal directing from the collecting part 160 toward the light receiving part 180 may be facilitated. Accordingly, a distance between the collecting part 160 and the light receiving part 180, that is, the second path L2 may be reduced, thereby achieving miniaturization of the airborne microorganism measurement device 100.

A process of measuring the airborne microorganisms by the various device s of the airborne microorganism measurement device 100 described above will be described below.

Figure 6:
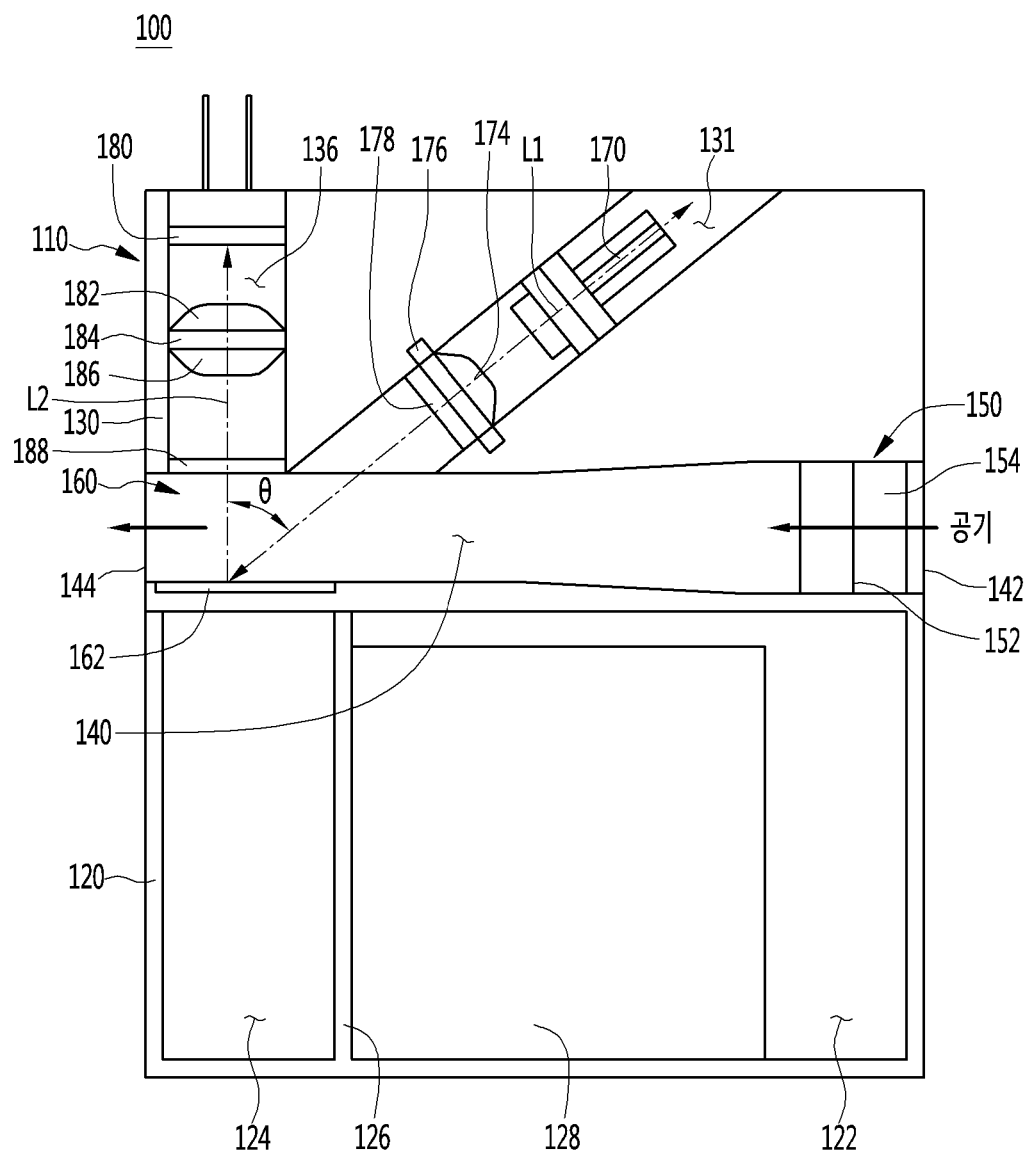
FIG. 6 is a plan view showing operation of a light emitting unit and a light receiving part of an airborne microorganism measurement device according to an embodiment of the present invention.

FIG. 6 is a plan view showing behavior of a light emitting unit 170 and a light receiving part 180 of the airborne microorganism measurement device 100 according to an embodiment of the present invention.

As described above, air containing airborne microorganisms is introduced into the first opening 142 and flows through the air passage 140. The airborne microorganisms charged by passing through the charging part 150 are collected in the collecting part 160 and placed on the collecting substrate 162.

The light emitting unit 70 irradiates light toward the collecting substrate 162 on which the airborne microorganisms are collected. The light irradiated from the light emitting unit 70 moves to the collecting substrate 162 in the first path L1 that passes through the light emitting lens 74 and the light emitting filter 78. The airborne microorganisms generate fluorescence signals due to the light. The generated fluorescence signals move to the light receiving part 180 in the second path L2 passing through the light receiving filter 188 and the first and second light receiving lenses 182 and 186 and the light receiving part 180 recognizes the fluorescence signals.

In this case, an angle between the first path L1 and the second path L2 may be referred to as a path angle θ. The path angle θ may be previously determined as forming a set angle. In other words, the path angle θ may be understood as being an angle between a first virtual line extending from the light emitting unit 170 toward one point of the collecting part 160 and a second virtual line extending from one point of the collecting part 160 toward the light receiving part 180.

Further, as described above, the path angle θ may be formed by the incident light passage 131 and the light receiving passage 136. It is noted that the incident light passage 131 and the light receiving passage 136 may be formed in a curved shape due to reasons such as manufacturing.

For example, the path angle θ may have a value of 55 degrees or more and 75 degrees or less. When the path angle θ is greater than 75 degrees, the light irradiated from the light emitting unit 70 greatly tends to be reflected by the collecting part 160 and move directly to the light receiving part 180, thereby causing a problem that the reception of the fluorescence signal generated from the riboflavin is reduced and the accuracy thereof is lowered.

When the path angle θ is less than 55 degrees, the light irradiated from the light emitting unit 70 greatly tends to be scattered from the collecting part 160, thereby causing a problem that the reception of the fluorescence signal generated from the riboflavin is reduced and the accuracy thereof is lowered.

Therefore, the present embodiment has the effect of limiting the path angle θ to a predetermined angle region, thereby improving the reception sensitivity of the fluorescent signal.

The airborne microorganism measurement device 100 may include various additional device s in addition to the device s for measuring airborne microorganisms. For example, the airborne microorganism measurement device 100 may not be installed in the air conditioner 10 but may be used as an independent device. Accordingly, a fan 190 for forcedly flowing air may be further included.

Further, a cleaning part 200 for removing airborne microorganisms collected on the collecting substrate 162 may be further included. Thereby, the collecting substrate 162 may be used repeatedly, thereby reducing a material cost and a measuring time.

Figure 7:
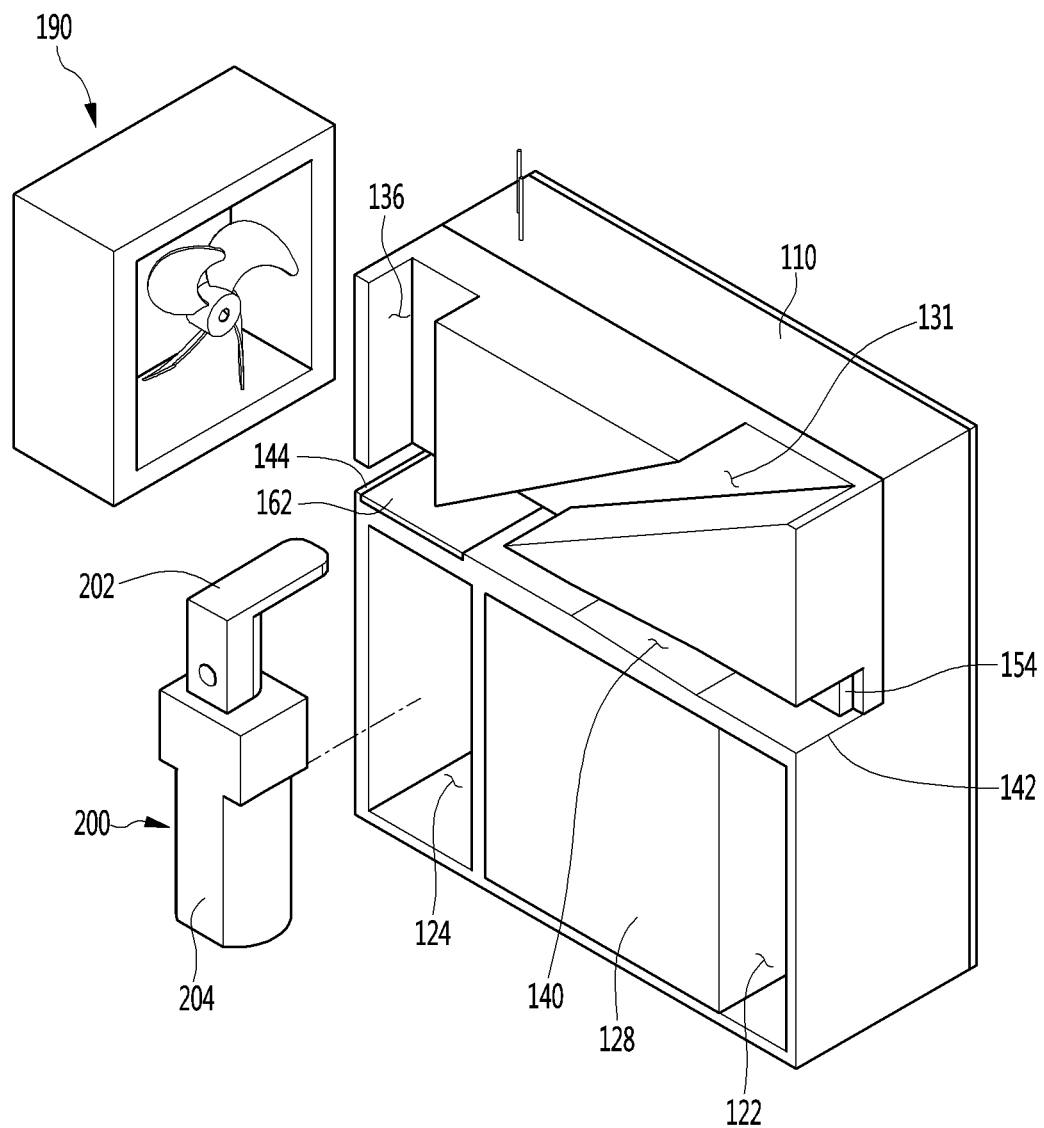
FIG. 7 is a perspective view illustrating a fan and a cleaning part of an airborne microorganism measurement device according to an embodiment of the present invention.

FIG. 7 is a perspective view illustrating a fan 190 and a cleaning part 200 of an airborne microorganism measurement device 100 according to an embodiment of the present invention.

The fan 190 may be installed adjacent to the second opening 144 to forcibly flow the air containing airborne microorganisms into the air passage 140. In detail, the fan 190 may be attached to one side of the housing 110 in which the second opening 144 is formed.

The fan 190 may be provided in various types for flowing air. In addition, the fan 190 may be installed so as not to interfere with light reflected from the collecting substrate 162.

As the fan 190 is included in the airborne microorganism measurement device 100, the airborne microorganism measurement device 100 may be used as an independent device and may be carried as an independent device Further, it also has an advantage that it may be installed and used in other device s that do not include a device such as a fan.

The cleaning part 200 may be disposed in the second space portion 124 adjacent to the collecting substrate 162. In detail, the cleaning part 200 includes a removing part 202 that moves in contact with the collecting substrate 162, and a motor 204 disposed in the second space portion 124 to transfer power to the removing part 202.

The motor 204 may be provided as a small motor so as to be installed in the second space portion 124. For example, the motor 204 includes a small DC geared motor and a stepping motor.

The removing part 202 is connected to the motor 204 installed in the second space portion 124 on one side and is disposed to abut the collecting substrate 162 that is disposed in the air passage 140 on the other side. That is, the removing part 202 is a region to extend from the second space portion 124 to the air passage 140.

The removing part 202 is rotated along the upper surface of the collecting substrate 162 by the driving force of the motor 204. In order to minimize damage to the collecting substrate 162, a material having a low abrasion rate and a function of removing particles excellently is attached to the removing part 202. For example, the removing part 202 includes a rubber fabric. In addition, the whole of the removing part 202 may be formed of a rubber fabric, and a part of the removing part 202, which is in contact with the collecting substrate 162, may be formed of a rubber fabric. For example, the rubber fabric may be Nitrile Butadiene Rubber (NBR).

Figure 8:
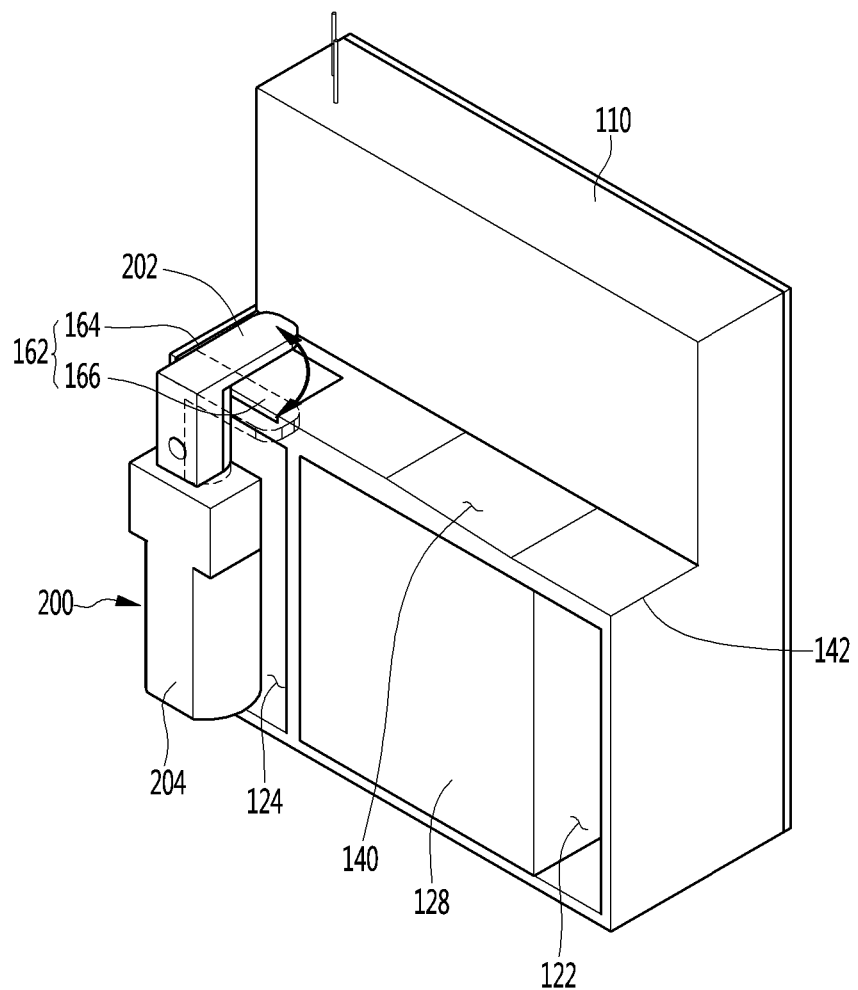
FIG. 8 is a perspective view illustrating operation of a cleaning part of an airborne microorganism measurement device according to the embodiment of the present invention.

FIG. 8 is a perspective view illustrating behavior of a cleaning part of an airborne microorganism measurement device according to the embodiment of the present invention.

As shown in FIG. 8, the removing part 202 may be arranged to move between a first side 164 and a second side 166 of the collecting substrate 162 to remove collected airborne microorganisms. Referring to FIG. 8, the first side 164 is the inside of the air passage 140 positioned adjacent to the second opening 144 and the second side 166 is the outside of the air passage 140 adjacent to the cover of the housing 110 (not shown).

For example, the removing part 202 is positioned on the second side 166 not to disturb measurement by the light emitting unit 170 and the light receiving part 180 when the airborne microorganisms are measured. In this case, the removing part 202 is positioned to protrude from the air passage 140 not to affect the path of light.

After the airborne microorganisms have been measured, the removing part 202 moves from the second side 166 to the first side 164 or from the first side 164 to the second side 166 and removes the airborne microorganisms that have been measured.

Further, a treating part (not shown) for treating the airborne microorganisms removed by the removing part 202 may be provided on at least one of the first side 164 and the second side 166. For example, the treating part may be provided in the form of having an internal space, and may be disposed on one side of the collecting substrate 162 or the motor 204.

Further, the removing part 202 may be coated with an antimicrobial agent to simultaneously remove and treat the airborne microorganisms. In addition, it is possible to remove the airborne microorganisms by irradiating light such as UV onto the removing part 202 or the collecting substrate 162

Figure 9:
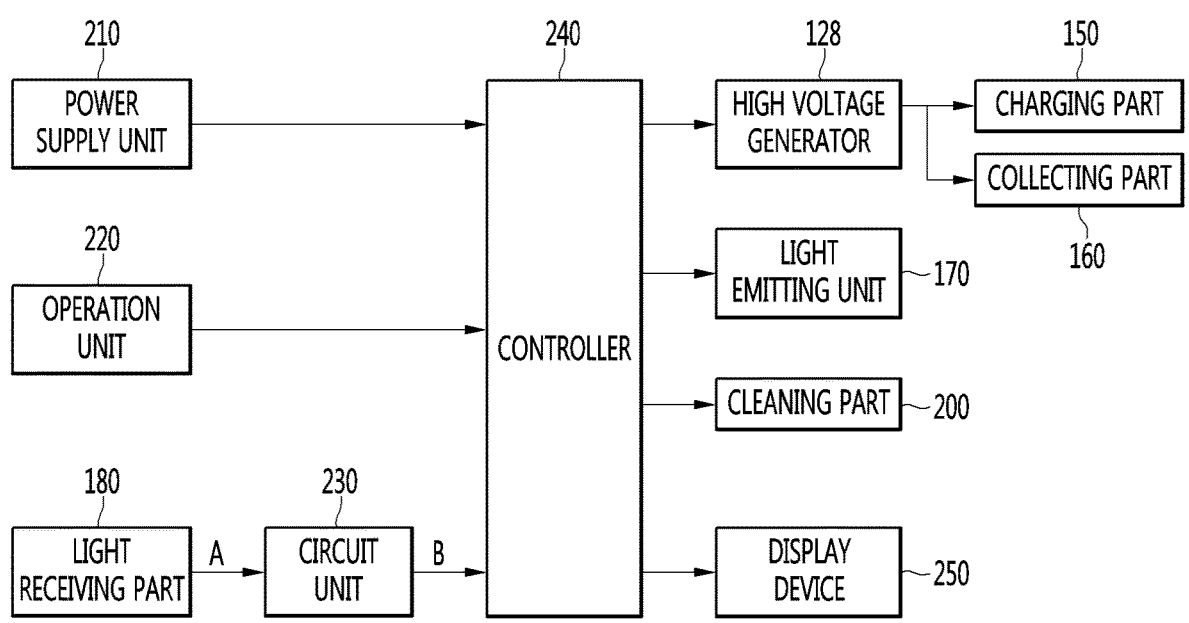
FIG. 9 is a control block diagram of an airborne microorganism measurement device according to an embodiment of the present invention.

FIG. 9 is a control block diagram of an airborne microorganism measurement device according to an embodiment of the present invention, and FIG. 10 is a control flowchart of an airborne microorganism measurement device according to an embodiment of the present invention.

The airborne microorganism measurement device 100 further includes a control unit 240 for controlling the various device s described above. As shown in FIG. 9, a power supply unit 210, an operation unit 220 having buttons and the like and the light receiving part 180 are connected to an input terminal of the control unit 240.

The high voltage generator 128, the light emitting unit 70, the cleaning part 200, and a display device 250 are connected to an output terminal of the control unit 240.

In this case, the control unit 240 may control the operations of the high voltage generator 128, the light emitting unit 170, and the cleaning part 200 according to preset times.

The power supply unit 210 may be separately provided in the airborne microorganism measurement device 100 or may be a power supply of an installed device such as the air conditioner 10. The operation unit 220 may be provided with various buttons or the like, and various modes and the like may be performed by a button pressing operation by a user.

The control unit 240 allows the high voltage generator 128 to apply high voltages to the charging part 150 and the collecting part 160 according to the input of the power supply unit 210 and the operation unit 220. Alternatively, the collecting substrate 162 may be cleaned by allowing the light emitting unit 70 to irradiate light of a specific wavelength or by controlling the cleaning part 200.

Further, a circuit unit 230 for amplifying a target signal received by the light receiving part 180 may be provided. The circuit unit 230 includes an amplifying circuit for amplifying an electric signal output from the light receiving part 180 by several ten thousands to several hundred millions of times. That is, it functions to convert the electric signal A from the light receiving part 180 into an amplified electric signal B. Accordingly, it is possible to analyze signals that may not be measured due to the simplification and miniaturization of the airborne microorganism measurement device 100.

The control unit 180 may recognize the amplified electric signal B and determine the amount or concentration of the airborne microorganisms stored in the collecting substrate 162. The control unit allows the display device 250 to display information on the amount or concentration of the airborne microorganisms.

The display device 250 may be provided as a separate device from the airborne microorganism measurement device 100 or may be a display device provided in another device provided with the airborne microorganism measurement device 100. The display device 250 may be connected to the control unit 180 in a wired or wireless manner to receive data. The information on the airborne microorganisms may be visually displayed on the display device 250 so that the user may conveniently identify the information.

For example, the display device 250 may display different colors depending on a concentration value of airborne microorganism particles or environmental cleanliness. For example, when the concentration of the airborne microorganisms is low or the environmental cleanliness is good, green is displayed. When the concentration and the cleanliness are intermediate, yellow is displayed. When the concentration is high or the cleanliness is bad, red may be displayed.

The operation of the airborne microorganism measurement device 100 according to an embodiment of the present invention will be described with reference to FIG. 10.

When a power supply is turned on, air containing airborne microorganisms is introduced through the first opening 142 of the air passage 140 (S10). In this case, the power supply includes a power supply of an apparatus provided with the airborne microorganism measurement device 100 such as the air conditioner 10 or a power supply of the airborne microorganism measurement device 100 itself. Accordingly, when the power supply is turned on, air is caused to flow by driving the blowing fan 60 of the air conditioner 10 or by driving the fan 190 of the airborne microorganism measurement device 100.

When the power supply is turned on, the control unit 240 allows the cleaning part 200 to clean the collecting substrate 162 (S20). In this case, the cleaning part 200 moves a predetermined number of times along the upper surface of the collecting substrate 162 to remove airborne microorganisms, dust, and the like remaining on the collecting substrate 162. For example, the removing part 202 may remove the airborne microorganisms by moving on the collecting substrate 162 three times.

After the cleaning is completed, the control unit 240 allow the high voltage generator 128 to apply high voltage to the charging part 150 and the collecting part 160. The charging part 150 charges the airborne microorganisms in the introduced air and the charged airborne microorganisms are collected in the collecting part 160 (S30).

In order to collect airborne microorganisms enough to be measured, the collection process may be continued for a predetermined time. For example, high voltage may be applied to the charging part 150 and the collecting part 160 for a predetermined time of minimum 30 minutes and maximum about 6 hours to collect the airborne microorganisms.

After the collecting of the airborne microorganisms is completed, the light is irradiated from the light emitting unit 70 toward the collecting part 160 (S40). Also, the light emitting unit 70 may irradiate light for a preset time. For example, the time to radiate the light may be set between 10 seconds and 60 seconds.

The irradiated light passes through the incident light lens 74 and the incident light filter 78 and is transferred to the collecting part 160. The transferred light acts on riboflavin of the airborne microorganism collected in the collecting part 160 to generate a fluorescence signal.

The fluorescence signal generated from the riboflavin passes through the light receiving filter 188 and the first and second light receiving lenses 182 and 186 to be transferred to the light receiving part 180 and the light receiving part 180 detects the transferred fluorescence signal (S50).

The fluorescence signal detected by the light receiving part 180 is amplified by the circuit unit 230 and transferred to the control unit 240. Accordingly, the control unit 240 may determine the amount or concentration of the airborne microorganisms collected in the collecting part 160.

For example, the control unit 240 may compare a measured value obtained by radiating light when the airborne microorganisms are not collected in the collecting part 160 and a measured value by radiating light when the airborne microorganisms are collected in the collecting part 160. When there is no difference between the measured values or there is a difference less than a preset value, it is determined as a safe state. When there is a difference between the measured values or there is a difference equal to or greater than the preset value, it is determined as a dangerous state.

The control unit 240 transmits information on the amount or concentration of the airborne microorganisms to the display device 250, and the display device 250 displays the information. For example, when the control unit 240 determines the safe state, a sentence or a color indicating the safe state may be displayed on the display device 250. When the control unit 240 determines the dangerous state, a sentence or a color representing the dangerous state may be displayed on the display device 250 and an air clean mode may be performed.

According to such a control method, the airborne microorganism measurement device having a simple structure operates each of steps at predetermined time intervals, thereby conveniently measuring airborne microorganisms in air and performing air cleaning accordingly.

In addition, the airborne microorganism measurement device of the present invention may be simplified and reduced in size by omitting unnecessary components. A configuration of an airborne microorganism measurement device 301 according to another embodiment will be described below with reference to the drawings.

Figure 11:
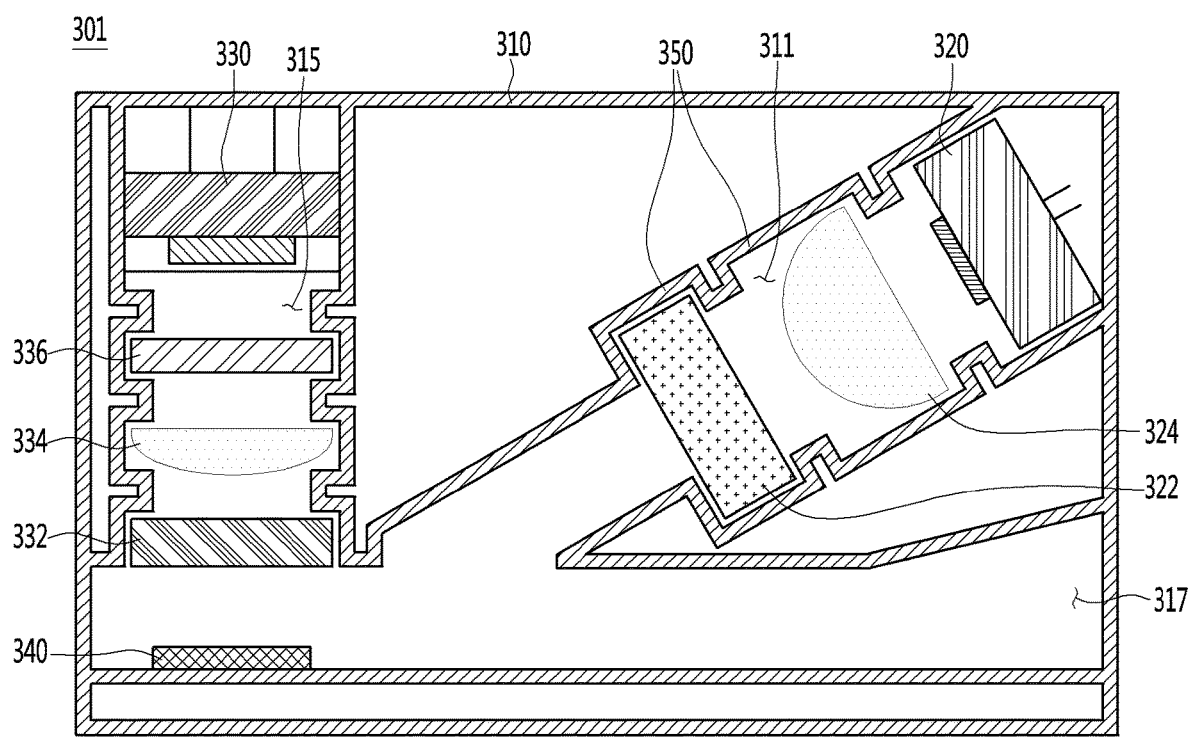
FIG. 11 is a schematic view showing a configuration of an airborne microorganism measurement device according to another embodiment of the present invention.

FIG. 11 is a schematic view showing a configuration of an airborne microorganism measurement device according to another embodiment of the present invention.

As shown in FIG. 11, the airborne microorganism measurement device 301 according to an embodiment of the present invention is provided with an optical housing 310 having a plurality of passages therein. The appearance of the optical housing 310 may have a rectangular shape with a predetermined thickness.

In particular, the appearance of the optical housing 310 may have a horizontal length of 35 to 40 mm and a vertical length of 20 to 30 mm. The lengths are determined by a focal length required for optical measurement and are very small as compared to conventional airborne microorganism measurement devices. Therefore, the optical housing 310 may be installed not only in another apparatus but also be used as a portable device.

An incident light passage 311 and a light receiving passage 315 are provided in the optical housing 310. The incident light passage 311 and the light receiving passage 315 are formed to extend in a straight line in the optical housing 310.

The incident light passage 311 and the light receiving passage 315 may form a predetermined path angle θ. That is, the incident light passage 311 and the light receiving passage 315 are arranged so as not to be parallel to each other to have an intersection.

The airborne microorganism measurement device 301 includes a light emitting unit 320, a measurement plate 340, and a light receiving part 330.

The light emitting unit 320 is installed in the incident light passage 311 to radiate light of a predetermined wavelength region. The light irradiated from the light emitting unit 320 is directed to the measurement plate 340.

The light emitting unit 320 includes a laser diode. The laser diode may emit light having a predetermined wavelength value or a wavelength region. For example, the predetermined wavelength value may be 405 nm and the wavelength region may be 395 to 415 nm.

The output of the laser diode may have a value equal to or less than a set output. When the output of the laser diode becomes too high, the measurement object received in the measurement plate 340 may be destroyed before measurement. For example, a set output value may be 20 mW.

The measurement plate 340 is disposed at an intersection of the incident light passage 311 and the light receiving passage 315. A measurement object that needs to be measured may be received in the measurement plate 340.

The measurement object may be collected directly on the measurement plate 340 or placed on the measurement plate

340. In addition, the measurement object may be accommodated to be measurable in the measurement plate 340 in various types.

For example, the measurement plate 340 may be provided as a substrate and a discharge electrode provided on a surface of the substrate. The substrate is an insulating substrate, for example, a sapphire wafer. Since the sapphire wafer has a hydrophobic property, moisture contained in air may be prevented from being collected on the wafer. Further, since the sapphire substrate has a very high hardness, its abrasion may be prevented.

The discharge electrode may be coated on the surface of the substrate. In detail, the discharge electrode may be provided on the surface of the substrate in a mesh type. Therefore, when the light irradiated from the light emitting unit 320 moves to the measurement plate 340, at least a part of the light may be transmitted through a surface on which the discharge electrode is not provided.

When high voltage is applied to the discharge electrode, a strong electric field is formed, and a corona discharge may be generated due to a voltage difference between the discharge electrode and the ground electrode. The negative (−) ions or positive (+) ions generated during the corona discharge are charged with the measurement object, and therefore, the measurement object may be charged. The charged measurement object may be collected in the measurement plate 340.

This is an example in which the measurement object is directly collected in the measurement plate 340. In addition, when previously-collected measurement object is placed on the measurement plate 340, the measurement plate 340 may be provided in the form of a simple flat plate.

However, the measurement plate 340 may be made of a material that transmits at least a part of transferred light. Therefore, at least a part of the light transmitted to the measurement plate 340 may be transmitted through the measurement plate 340.

When the measurement plate 340 is made of a material through which light is not capable of being transmitted, the light transferred to the measurement plate 340 may be entirely reflected or scattered, which may restrict accurate detection of a target signal.

The measurement object generates a target signal by the light irradiated from the light emitting unit 320. In this case, the target signal may be a fluorescence signal of riboflavin.

Specifically, the measurement object includes riboflavin. The riboflavin may be understood as a coenzyme contained in a microorganism.

That is, a predetermined wavelength region of light irradiated from the light emitting unit 320 is a wavelength rang in which a strong condensed beam may be obtained, and may be understood as a wavelength region determined to increase a biological fluorescence signal generated by acting on the riboflavin.

As described above, the fluorescence signal is realized by using the absorption or luminescence phenomenon of the riboflavin contained in the measurement object, thereby requiring no separate fluorescence treatment for the measurement object.

In other words, the riboflavin contained in the measurement object generates a target signal in a specific wavelength region due to the light irradiated from the light emitting unit 320

The light receiving part 330 is disposed in the light receiving passage 315 to detect the target signal. That is, the target signal generated from the measurement plate 340 is directed to the light receiving part 330.

The light receiving part 330 includes an element that receives the fluorescence signal of the riboflavin and has high sensitivity to light of a predetermined wavelength value or wavelength region.

The predetermined wavelength value or wavelength region may be a value or region determined to detect only an emission wavelength band of riboflavin contained in the measurement object and not to measure scattered light or the like of fine dust contained in air. For example, the predetermined wavelength value may be 565 nm, and the wavelength region may be 555 to 575 nm.

For example, the light receiving part 180 includes a photodiode, and the photodiode has a relatively short reaction time.

In addition, the photodiode may read a fluorescent signal having a wavelength band of 565 nm, and an element having a smaller noise at the same input value may be used. In this case, rise and fall times, bias voltage, dark current and the like may be considered.

A path in which light irradiated from the light emitting unit 320 to the measurement plate 340 is directed is referred to as a 'first path'. A path in which a target signal from the measuring plate 340 to the light receiving part 330, that is, reflected light is directed is referred to as a 'second path'.

The first path and the second path may form a predetermined path angle θ. This is the same as the predetermined path angle θ formed by the incident light passage 311 and the light receiving passage 315 described above.

The predetermined path angle θ is provided at an acute angle. That is, the predetermined path angle θ is designed to be smaller than 90 degrees.

when the path angle θ is at an angle larger than 90 degrees, that is, at a right angle or an obtuse angle, the light irradiated from the light emitting unit 320 greatly tends to be reflected by the measurement plate 340 to directly travel to the light receiving part 330. Therefore, there is a problem that the reception of the target signal generated from the measurement object is reduced and the accuracy thereof is lowered.

Therefore, the present embodiment has the effect of limiting the path angle θ to a predetermined angle region, thereby improving the reception sensitivity of the fluorescent signal.

The surfaces of the incident light passage 311 and the light receiving passage 315 may be oxidized to prevent reflection of light. Specifically, an inner surface of the optical housing 310 through which light travels may be provided with an oxidized metal.

Oxidation treatment makes the surface matte and dark so that diffused light is absorbed without reflection. Since the diffused light is not reflected again, it does not affect the first path and the second path, thereby achieving more accurate measurement results.

The airborne microorganism measurement device 301 may further include an incident light filter 322 and an incident light lens 324 disposed between the light emitting unit 320 and the measurement plate 340.

The incident light lens 324 may be installed on one side of the light emitting unit 320. The incident light lens 324 may be referred to as a "condensing lens" and may collect light irradiated from the light emitting unit 320.

For example, the light irradiated from the light emitting unit 320 has a divergence angle of about 10 degrees, and thus the light irradiated from the light emitting unit 320 has a gradually diverging path while traveling toward the measurement plate 340. Accordingly, the incident light lens 324 may be provided on the exit side of the light emitting unit 320 to make light directed to the measurement plate 340 parallel.

In this case, the incident light lens 324 is spaced apart from the light emitting unit 320 by a predetermined distance so as to effectively collect the light irradiated from the light emitting unit 320. For example, an interval between the light emitting unit 320 and the incident light lens 324 may be set to a distance over which light on the measurement plate 340 is clearly visible.

The incident light filter 322 may be installed on one side of the incident light lens 324. For example, the incident light filter 322 may be installed on the light exit side of the incident light lens 324, that is, at a position where light having passed through the incident light lens 324 may pass through.

The incident light filter 322 may function to pass only light of a predetermined wavelength region among the light irradiated from the light emitting unit 320. When light outside the predetermined wavelength region (395-415 nm) is irradiated from the light emitting unit 320, the light may be filtered out so such that only light of the predetermined wavelength region passes through in the course of passing through the incident light filter 322. The incident light filter 322 may be referred to as a "laser line filter".

In this case, the incident light filter 322 and the incident light lens 324 are disposed in the incident light passage 311. As shown in FIG. 11, the incident light filter 322, the incident light lens 324, and the light emitting unit 320 are sequentially disposed in the incident light passage 311.

The airborne microorganism measurement device 301 may further include a plurality of light receiving filters 332 and 336 and a light receiving lens 334 disposed between the measurement plate 340 and the light receiving part 330.

The light receiving filters 332 and 336 are provided such that the target signal generated from the measurement object is able to pass therethrough. That is, it functions to block a signal other than the target signal.

For example, the light receiving filters 332 and 336 may function to prevent the wavelength region of the light irradiated from the light emitting unit 320 from passing therethrough. Therefore, among the light irradiated from the light emitting unit 320, light that is reflected by the measurement plate 340 and travels may be filtered while passing through the light receiving filters 332 and 336. The light receiving filters 332 and 336 may be referred to as "long pass filters".

The light receiving filters include a first light receiving filter 332 for passing light of a first wavelength or longer and a second light receiving filter 336 for passing light of a second wavelength or longer.

In this case, the first wavelength and the second wavelength are in different wavelength bands.

For example, the second wavelength may be longer than the first wavelength. For example, the first wavelength may be 442 nm, or may have a wavelength region of 432 nm to 452 nm, and the second wavelength may be 500 nm or may have a wavelength region of 490 nm to 510 nm.

The light receiving lens 334 is disposed between the first light receiving filter 332 and the second light receiving filter 336. The light receiving lens 334 may be a condensing lens and may be composed of the same kind of lens as the incident light lens 324.

The first light receiving filter 332 is provided on one side of the measurement plate 340 and the light receiving lens 334 is provided on one side of the first light receiving filter 332. Further, the second light receiving filter 336 is provided on one side of the light receiving lens 334 and the light receiving part 330 is provided on one side of the second light receiving filter 336.

That is, light reflected by the measurement plate 340 is filtered once by the first light receiving filter 332, and light collected by the light receiving lens 334 is filtered again by the second light receiving filter 336.

The light that has not been filtered by the first light receiving filter 332 by diffused reflection may be filtered by the second light receiving filter 336 as the light is condensed by the light receiving lens 334. Accordingly, it is possible to more accurately measure the target signal to be measured by the light receiving part 330.

In this case, the first and second light receiving filters 332 and 336 and the light receiving lens 334 are disposed inside the light receiving passage 315. Accordingly, as shown in FIG. 11, the first light receiving filter 332, the light receiving lens 334, the second light receiving filter 336, and the light receiving part 330 are sequentially disposed in the light receiving passage 315.

That is, the measurement plate 340 is disposed at the intersection of the incident light passage 311 and the light receiving passage 315, and the incident light filter 322, the incident light lens 324, and the light receiving part 320 are sequentially disposed adjacent to the measurement plate 340 in the incident light passage 311, and the first light receiving filter 332, the light receiving lens 334, the second light receiving filter 336, and the light receiving part 330 are sequentially disposed adjacent to the measurement plate 340 in the light receiving passage 315. Each of the configurations may be arranged in turn to space apart from one another at predetermined intervals.

The incident light passage 311 and the light receiving passage 315 are provided with a plurality of mounting grooves 350 in which the light emitting unit 320, the incident light filter 322, the incident light lens 324, the first light receiving filter 332, the light receiving lens 334, the second light receiving filter 35, and the light receiving part 330 are mounted.

The plurality of mounting grooves 350 may be spaced apart from one another at predetermined intervals in the incident light passage 311 and the light receiving passage 315. Each of the mounting grooves 350 may be formed to protrude outward from the incident light passage 311 and the light receiving passage 315. That is, a portion where the mounting groove 350 is provided has a wider cross-sectional area than that where it is not provided.

The light emitting unit 320, the incident light filter 322, the incident light lens 324, the first light receiving filter 332, the light receiving lens 334, the second light receiving filter 336, and the light receiving part 330 may be respectively fitted or assembled to the mounting grooves.

In addition, the optical housing 310 may be further formed with an air passage 317 through which air containing the measurement object flows. The air passage 317 is provided to allow the measurement object to be collected in the measurement plate 340.

As shown in FIG. 11, the air passage 317 is formed to extend linearly in the optical housing 310 so as to meet the incident light passage 311 and the light receiving passage 315 at the intersection in which the measurement plate 340 is disposed.

As described above, the measurement object may be collected by the measurement plate 340 or may be received in the measurement plate 340 in the collected state. The airborne microorganism measurement device 310 provided with the air passage 317 is illustrated in FIGS. 11 to 14, and a case where a measurement object is collected by the measurement plate 340 will be described.

A measurement method by the airborne microorganism measurement device 301 will be described below in detail.

Figure 12:
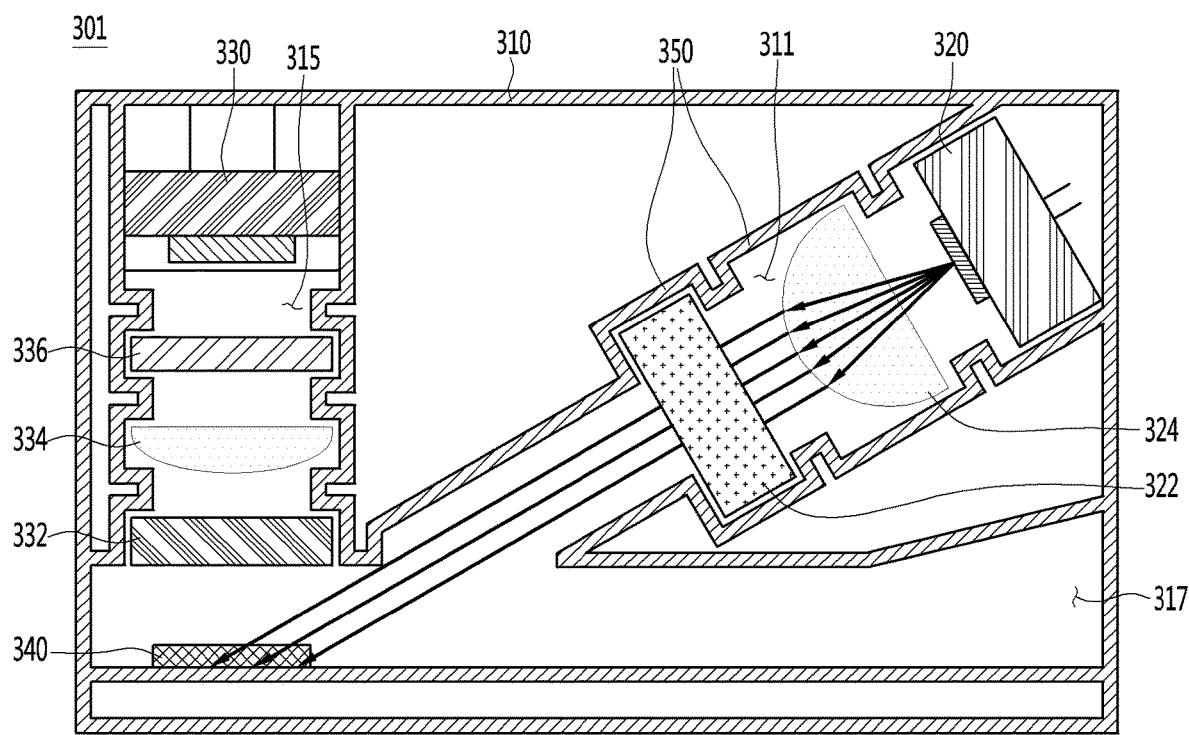
FIG. 12 is a schematic view showing a path of light from a light emitting unit to a measurement plate in an airborne microorganism measurement device according to another embodiment of the present invention.

FIG. 12 is a schematic view showing a path of light to a measurement plate from a light emitting unit of an airborne microorganism measurement device according to another embodiment of the present invention.

Air containing the measurement object is introduced through the air passage 317 and the measurement target is collected in the measurement plate 340. As described above, the measurement object in the air may be charged and collected by corona discharge generated by applying high voltage to a discharge electrode provided in the measurement plate 340.

Subsequently, the light emitting unit 320 operates to radiate light of a predetermined wavelength region. The irradiated light passes through the incident light lens 324 and the incident light filter 322 and is transferred to the measurement plate 340.

At least a part of the light may be transmitted through the measurement plate 340 to travel and another part may be reflected by the measurement plate 340.

At least a part of the light transferred to the measurement plate 340 acts on the riboflavin contained in the measurement object accommodated in the measuring plate 340. Accordingly, the measurement object generates a fluorescence signal, that is, a target signal to be measured.

Figure 13:
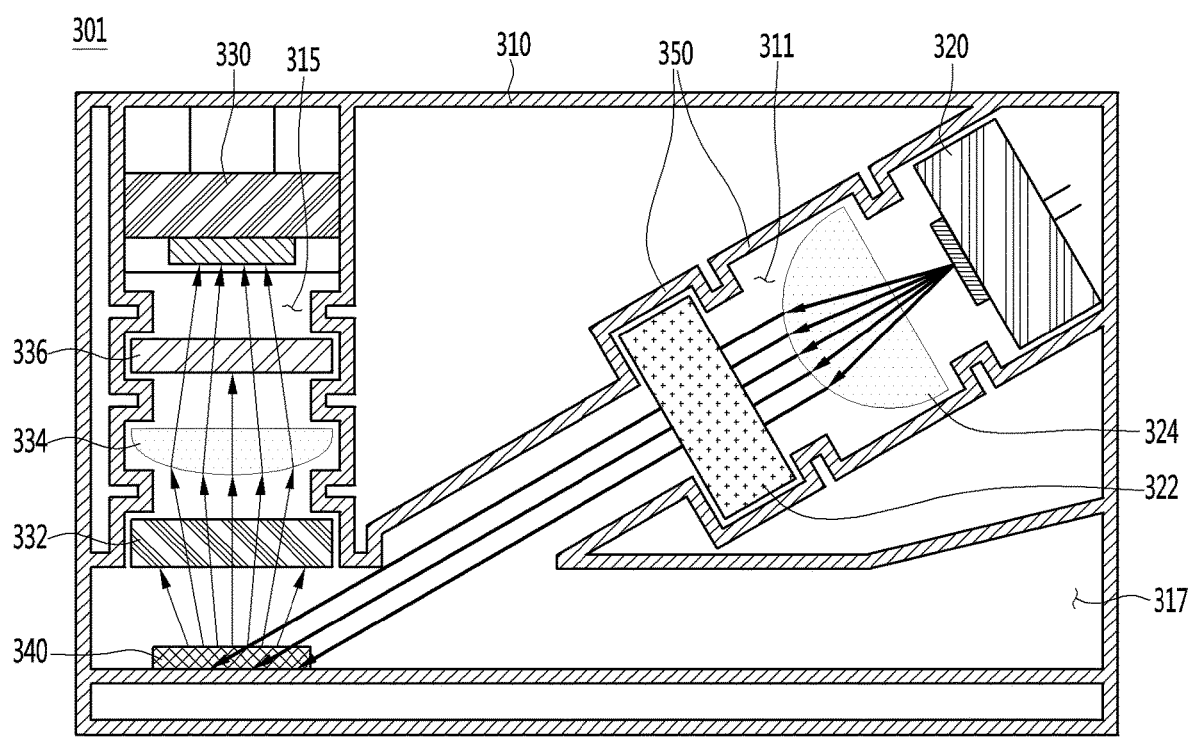
FIG. 13 is a schematic view showing a path of light from a measurement plate to a light receiving part in an airborne microorganism measurement device according to another embodiment of the present invention.

FIG. 13 is a schematic view showing a path of light from a measurement plate to a light receiving part in an airborne microorganism measurement device according to another embodiment of the present invention.

The target signal is transferred to the light receiving passage 315 and is transferred to the light receiving part 330 through the first light receiving filter 332, the light receiving lens 334 and the second light receiving filter 336.

As described above, reflected light other than the target signal is filtered out by the first light receiving filter 332 and the second light receiving filter 336. It is possible to measure the target signal more accurately in the light receiving part 330 by being filtered by a plurality of light receiving filters.

Figure 14:
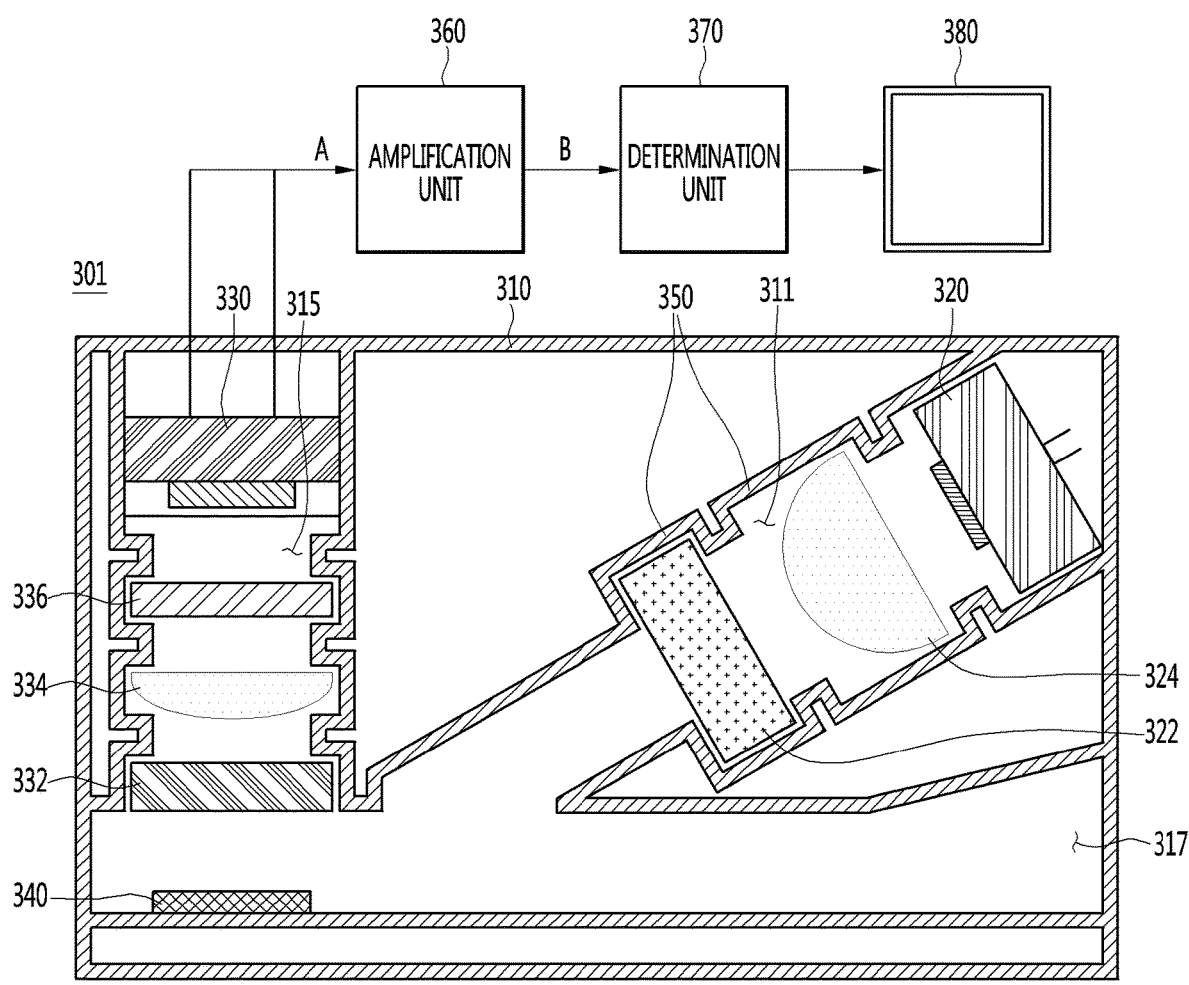
FIG. 14 is a diagram illustrating an amplification unit and a determination unit of an airborne microorganism measurement device according to another embodiment of the present invention.

FIG. 14 is a diagram illustrating an amplification unit and a determination unit of an airborne microorganism measurement device according to another embodiment of the present invention.

The airborne microorganism measurement device 301 may further include an amplification unit 360 that amplifies a target signal received by the light receiving part 330.

The amplification unit 360 amplifies and output an electric signal output from the light receiving part 330 by several ten thousands to several hundred millions of times. That is, it functions to convert the electric signal A from the light receiving part 330 into an amplified electric signal B.

Accordingly, it is possible to analyze a target signal that may not be measured due to the simplification and miniaturization of the airborne microorganism measurement device 100.

The airborne microorganism measurement device 301 may further include a determination unit 370 for outputting and analyzing a target signal received by the light receiving part 330.

The determination unit 370 may determine the amount or concentration of the measurement object accommodated in the measurement plate 340 by recognizing the amplified electric signal B. That is, the determination unit 370 determines the concentration or environmental cleanliness of the measurement object by analyzing the measured target signal.

For example, the determination unit 370 may determine the concentration of microorganisms or the environmental cleanliness through a correlation regression analysis between the fluorescence signal and the concentrations of microorganisms and bio-derived substances in atmospheric environment.

In addition, the airborne microorganism measurement device 301 may include a display device 380 that displays information on the amount or concentration of the measurement object from the target signal.

The display device 380 may be provided separately from the airborne microorganism measurement device 301. The display device 380 may be connected to the determination unit 370 in a wired or wireless manner to receive data. The user may easily identify the information on the measurement object by visually displaying the information on the display device 380.

For example, the display device 380 may display different colors depending on a concentration value of measurement object particles or environmental cleanliness. For example, when the concentration of the measurement object is low or the environmental cleanliness is good, green is displayed. When the concentration and the cleanliness are intermediate, yellow is displayed. When the concentration is high or the cleanliness is bad, red may be displayed.

The airborne microorganism measurement device 301 may be installed in another product to transmit data. For example, it may be installed on an air cleaner to transfer information on the measurement object to a display unit of the air cleaner to be visualized.

As shown in FIGS. 11 to 14, the airborne microorganism measurement device 301 may be provided with a rectangular optical housing 310. However, this is merely an example, and the airborne microorganism measurement device 301 may be provided in various shapes. Another example will be described below.

Figure 15:
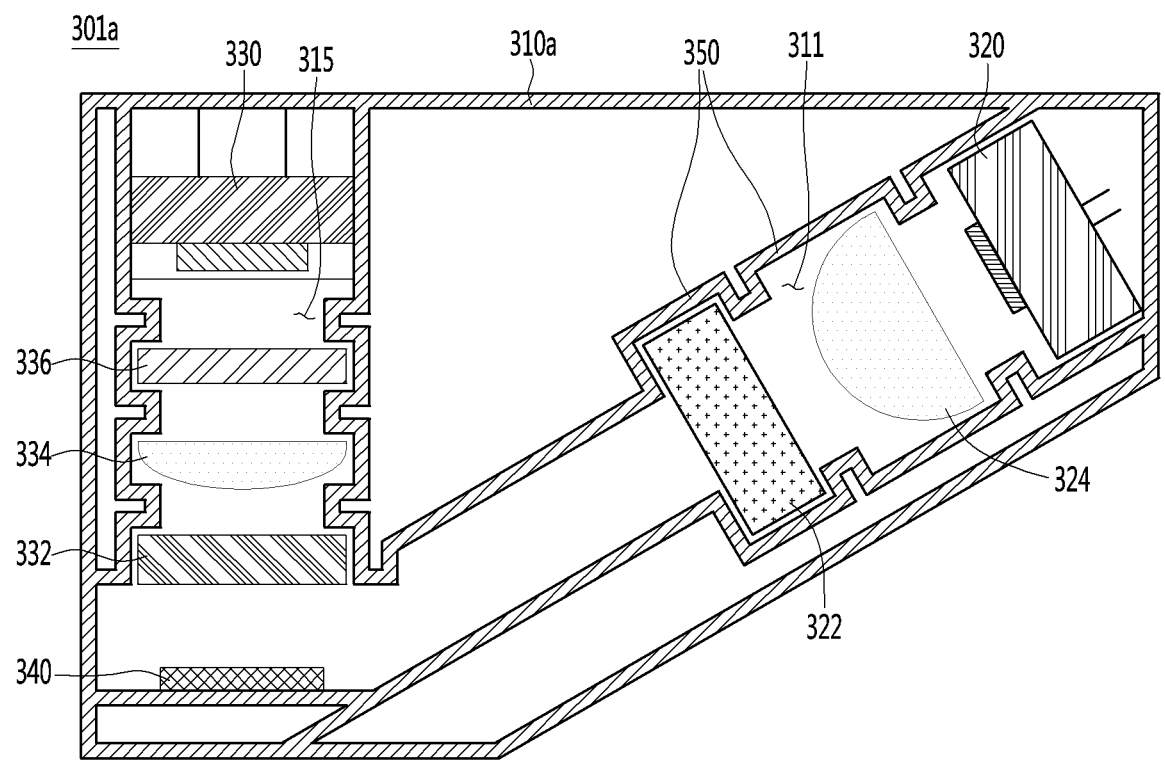
FIG. 15 is a schematic view showing a configuration of an airborne microorganism measurement device according to still another embodiment of the present invention.

FIG. 15 is a schematic view showing a configuration of an airborne microorganism measurement device according to still another embodiment of the present invention.

An airborne microorganism measurement device 1a shown in FIG. 15 has the same configuration as the airborne microorganism measurement device 301 described above except for the air passage 317. The description of the airborne microorganism measurement device 301 described above is referred to with respect to same part and only the difference will be described below.

The airborne microorganism measurement device 301a is provided with an optical housing 10a having a substantially triangular shape and having a predetermined thickness. The optical housing 310a is provided with the incident light passage 311 and the light receiving passage 315 which form a predetermined path angle θ.

The path angle θ may be at an acute angle, and the incident light passage 311 and the light receiving passage 315 may be formed in a triangular shape. As described above, since the path angle θ is provided at an acute angle, the reception sensitivity of the target signal may be improved.

In other words, the incident light passage 311, the light receiving passage 315, a straight line intersecting the incident light passage 311 and the light receiving passage 315 form a triangle. Accordingly, the optical housing 310a is provided in a triangular shape.

By omitting all other configurations than the incident light passage 311 and the light receiving passage 315, the airborne microorganism measurement device 301a may be reduced in overall size thereof and simplified. Accordingly, it is easy to facilitate installation in a required space, and the airborne microorganism measurement device 301 may be installed in an unnecessary space existing in an apparatus such as an air conditioner.

Therefore, the airborne microorganism measurement device according to an embodiment of the present invention may measure a measurement object with a simplified and miniaturized apparatus.

The invention claimed is:

1. An airborne microorganism measurement device comprising:
    a housing including a first body and a second body defined by a plurality of walls, the second body being spaced apart to a side of the first body;
    an air passage formed between the first body and the second body such that air containing airborne microorganisms pass therethrough;
    a charger and a collector disposed in the air passage to charge and collect the airborne microorganisms;
    a high voltage generator provided in the first body to supply a high voltage to the charger and the collector; and
    a light emitter and a light receiver provided in the second body to detect a fluorescent signal generated by irradiating the airborne microorganisms collected in the collector with light.

2. The airborne microorganism measurement device of claim 1, wherein the charger is disposed adjacent to a first opening of the air passage into which the air containing the airborne microorganisms is introduced, and wherein the collector is disposed adjacent to a second opening of the air passage to collect the airborne microorganisms charged by the charger.

3. The airborne microorganism measurement device of claim 1, wherein the collector includes a collecting substrate connected to the high voltage generator and disposed in the air passage abutting the first body.

4. The airborne microorganism measurement device of claim 3, wherein the collecting substrate is made of a glass member having electrical conductivity.

5. The airborne microorganism measurement device of claim 3, further comprising a cleaner having at least a portion disposed in the first body to remove the airborne microorganisms collected in the collector.

6. The airborne microorganism measurement device of claim 5, wherein the first body includes a first space and a second space, wherein the high voltage generator is disposed in the first space, and wherein the at least a portion of the cleaner is disposed in the second space.

7. The airborne microorganism measurement device of claim 6, wherein the first space is positioned adjacent to the charger, and the second space is positioned adjacent to the collector.

8. The airborne microorganism measurement device of claim 6, wherein a separating wall separates the first space from the second space.

9. The airborne microorganism measurement device of claim 5, wherein the cleaner includes a remover configured to move in contact with the collecting substrate, and a motor configured to transfer power to the remover.

10. The airborne microorganism measurement device of claim 9, wherein the remover is arranged to move between a first side and a second side of the collecting substrate to remove the collected airborne microorganisms.

11. The airborne microorganism measurement device of claim 10, wherein at least one of the first side and the second side includes a treatment device that treats the airborne microorganisms removed by the remover.

12. The airborne microorganism measurement device of claim 10, wherein the remover includes a material having a low abrasion rate configured to move in contact with the collecting substrate to remove the collected airborne microorganisms.

13. The airborne microorganism measurement device of claim 10, wherein the motor is a DC geared motor or a stepper motor.

14. The airborne microorganism measurement device of claim 1, wherein the charger includes a high voltage wire connected to the high voltage generator and a pair of ground plates facing each other with the high voltage wire as a center.

15. The airborne microorganism measurement device of claim 1, wherein the second body is formed with an incident light passage and a light receiving passage which are connected to the air passage, wherein the light emitter is disposed in the incident light passage, and wherein the light receiver is disposed in the light receiving passage.

16. The airborne microorganism measurement device of claim 15, wherein the incident light passage is formed along a first path of light directed from the light emitter toward one point of the collector, and wherein the light receiving passage is formed along a second path of a fluorescent signal directed from the one point of the collector toward the light receiver.

17. The airborne microorganism measurement device of claim 16, wherein the first path and the second path form a predetermined path angle.

18. An air conditioning device comprising the airborne microorganism measurement device according to claim 1.

19. The air conditioning device of claim 18, wherein the microorganism measurement device is provided inside an airborne microorganism measurement device case, and wherein the airborne microorganism measurement device case is installed on one side of a filter of the air conditioning device.

20. The air conditioning device of claim 19, wherein the airborne microorganism measurement device case includes an air inflow portion through which at least a portion of air passing through the filter is introduced and an outflow portion through which the air is discharged.

* * * * *